US010159675B2

(12) United States Patent
Hagner et al.

(10) Patent No.: US 10,159,675 B2
(45) Date of Patent: *Dec. 25, 2018

(54) CYCLING THERAPY USING 3-(5-AMINO-2-METHYL-4-OXO-4H-QUINAZOLIN-3-YL)-PIPERIDINE-2,6-DIONE

(71) Applicant: Celgene Corporation, Summit, NJ (US)

(72) Inventors: Patrick Hagner, Sparta, NJ (US); Anita Gandhi, Bernardsville, NJ (US); Michael Pourdehnad, San Francisco, CA (US)

(73) Assignee: Celgene Corporation, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/367,117

(22) Filed: Dec. 1, 2016

(65) Prior Publication Data

US 2017/0157123 A1 Jun. 8, 2017

Related U.S. Application Data

(60) Provisional application No. 62/262,263, filed on Dec. 2, 2015.

(51) Int. Cl.
| | | |
|---|---|---|
| A61K 31/517 | (2006.01) | |
| A61P 35/00 | (2006.01) | |
| A61K 9/00 | (2006.01) | |

(52) U.S. Cl.
CPC .......... *A61K 31/517* (2013.01); *A61K 9/0053* (2013.01); *A61P 35/00* (2018.01)

(58) Field of Classification Search
CPC .................................................. A61K 31/517
See application file for complete search history.

(56) References Cited

U.S. PATENT DOCUMENTS

| | | | |
|---|---|---|---|
| 7,468,363 B2 | 12/2008 | Zeldis | |
| 7,498,171 B2 | 3/2009 | Hariri et al. | |
| 7,635,700 B2 | 12/2009 | Muller et al. | |
| 8,802,685 B2 | 8/2014 | Muller et al. | |
| 8,906,932 B2 | 12/2014 | Muller et al. | |
| 8,921,385 B2 | 12/2014 | Muller et al. | |
| 9,249,121 B2 | 2/2016 | Muller et al. | |
| 2003/0133939 A1 | 7/2003 | Ledbetter et al. | |
| 2005/0238646 A1 | 10/2005 | Ledbetter et al. | |
| 2012/0230983 A1* | 9/2012 | Muller | A61K 45/06 424/133.1 |
| 2014/0148473 A1 | 5/2014 | Gandhi et al. | |
| 2014/0162282 A1* | 6/2014 | Schafer | G01N 33/5047 435/7.1 |
| 2015/0196562 A1 | 1/2015 | Bhat | |
| 2015/0080419 A1 | 3/2015 | Muller et al. | |
| 2015/0126538 A1 | 5/2015 | Muller et al. | |
| 2016/0136167 A1 | 5/2016 | Gandhi et al. | |
| 2016/0214957 A1 | 7/2016 | Muller et al. | |
| 2017/0056323 A1 | 3/2017 | Walters et al. | |
| 2017/0128448 A1* | 5/2017 | Pourdehnad | A61K 39/39558 |

FOREIGN PATENT DOCUMENTS

| | | |
|---|---|---|
| WO | WO 2002/032925 A2 | 4/2002 |
| WO | WO 2002/088171 A2 | 11/2002 |
| WO | WO 2005/037989 A2 | 4/2005 |
| WO | WO 2006/055689 A2 | 5/2006 |
| WO | WO 2012/125459 A1 | 9/2012 |
| WO | WO 2016/007854 A1 | 1/2016 |
| WO | WO 2017/004532 A1 | 1/2017 |

OTHER PUBLICATIONS

Carpio et al., "CC-122 dosing on a novel intermittent schedule mitigates neutropenia and maintains clinical activity in subjects with relapsed or refractory diffuse large B cell lymphoma," Blood, 126:1494 (2015).
Clarke et al., "Changing incidence of non-Hodgkin lymphomas in the United States," Cancer, 94(7):2015-2023 (2002).
Jemal et al., "Cancer Statistics," CA Cancer J. Clin., 57:43-66 (2007).
Kim et al., "Use of absolute lymphocyte counts to predict response to chemotherapy and survival in diffuse large B-cell lymphoma," J. Clin. Oncology, ASCO Annual Meeting Proceedings Part I., 25(18S), Jun. 20 Supplement, p. 8082 (2007).
Ribrag et al., "CC-122 degrades the lymphoid transcription factor aiolos (IKZF3) by modulating cereblon and shows clinical activity in a phase 1b study of subjects with relapsed or refractory non-hodgkin's lymphoma and multiple myeloma," Blood, 124:3500 (2014).
Stahnke et al., "Activation of apoptosis pathways in peripheral blood lymphocytes by in vivo chemotherapy," Blood, 98:3066-3073 (2001).
Therasse et al., "New guidelines to evaluate the response to treatment in solid tumors," J. Natl. Cancer Inst., 92(3):205-216 (2000).
Gandhi et al., "CC-122 expands activated and memory CD4 and CD8 T cells in vivo and induces T cell activation ex vivo in subjects with relapsed or refractory diffuse large B cell lymphoma and mulitple myeloma," Blood, 126:2704 (2015).
Hagner et al., "CC-122 exhibits greater preclinical activity in mantle cell lymphoma than lenalidomide through a combination of direct cell-autonomous and increased antibody dependent cell-mediated cytotoxicity," Blood, 128:4188 (2016).
Hagner et al., "CC-122, a pleiotropic pathway modifier, mimics an interferon response and has antitumor activity in DLBCL," Blood, 126(6):779-789 (2015).
NCT01421524: "Study of CC-122 to evaluate the safety, tolerability, and effectiveness for patients with advanced solid tumors, non-hodgkin's lymphoma, or multiple myeloma," retrieved on Apr. 2, 2018, retrieved from the interent: URL:https://www.clinicaltrials.gov/ct2/show/record/NCT01421524 (Mar. 1, 2018).

(Continued)

*Primary Examiner* — Theodore R. West
(74) *Attorney, Agent, or Firm* — Jones Day

(57) ABSTRACT

Provided herein are methods of treating, preventing and/or managing cancer, including lymphoma, which comprise administering to a patient 3-(5-amino-2-methyl-4-oxo-4H-quinazolin-3-yl)-piperidine-2,6-dione, or an enantiomer or a mixture of enantiomers thereof, or a pharmaceutically acceptable salt, solvate, hydrate, co-crystal, clathrate, or polymorph thereof in a cyclic therapy regimen.

22 Claims, 7 Drawing Sheets

(56) References Cited

OTHER PUBLICATIONS

NCT02031419: "Novel combinations of CC-122, CC-223, CC-292, and Rituximab in diffuse large B-cell lymphoma," retrieved on Apr. 2, 2018, retrieved from the internet:URL:https://www.clinicaltrials.gov/ct2/show/record/NCT02031419 (Dec. 8, 2017).

NCT02406742: "A phase ½, open-label, dose finding study dto evaluate CC-122 in combination with ibrutinib and obinutuzumab in subjects with chronic lymphocytic leukemia/small lymphocytic lymphoma (ENHANCE)," retrieved on Apr. 2, 2018, retrieved from the internet: URL:http://www.clinicaltrials.gov/ct2/show/record/NCT02406742 (Nov. 30, 2017).

NCT02417285: "A phase 1b open-label study to evaluate the safety and efficacy of CC-122 with obinutuzumab (GA101) in relapse/refactory DLBCL and iNHL," retrieved on Apr. 2, 2018, retrieved from the internet: URL:https://www.clinicaltrials.gov/ct2/show/record/NCT02417285 (Dec. 18, 2017).

NCT02859324: "A safety and efficacy study of CC-122 in combination with nivolumab in subjects with unresectable hepatocellular carcinoma (HCC)," retrieved on Apr. 2, 2018, retrieved from the interent: URL:https://www.clinicaltrials.gov/ct2/show/record/NCT02859324 (Jun. 20, 2017).

Rasco et al., "A first in human dose escalation study of CC-122, a first-in-class pleiotropic pathway modulator™ (PPM) compound in subjects with relapsed or refractory solid tumors, multiple myeloma and non-hodgkin's lymphoma," *Blood*, 122:2905 (2013).

Ribrag et al., "A phase 1b, multi-center, open-label study of novel combinations of CC-122, CC-223, CC-292, and rituximab in diffuse large B-cell lymphoma: CC-122-DLBCL-001," *Blood*, 128:1849 (2016).

Ribrag et al., "CC-122 degrades the lymphoid transcription factor aiolos (IKZF3) by modulating cereblon and shows clinical activity in a phase 1b study of subjects with relapsed or refractory non-hodgkin's lymphoma and multiple myeloma," *Blood*, 124:3500 (2014).

* cited by examiner

CYCLING THERAPY USING 3-(5-AMINO-2-METHYL-4-OXO-4H-QUINAZOLIN-3-YL)-PIPERIDINE-2,6-DIONE

CROSS REFERENCE TO RELATED APPLICATIONS

This application claims the benefit of the priority of U.S. Provisional Application No. 62/262,263, filed Dec. 2, 2015, the disclosure of which is incorporated herein by reference in its entirety.

1. FIELD OF THE INVENTION

Provided herein are methods of treating, preventing, and/or managing cancer, including lymphoma such as diffuse large B-cell lymphoma (DLBCL), and preventing or reducing adverse effects associated with treating, preventing, managing, or ameliorating of such diseases by administering a compound of formula I or a pharmaceutically acceptable salt, solvate, hydrate, stereoisomer, tautomer or racemic mixtures thereof (Compound 1), including 3-(5-amino-2-methyl-4-oxo-4H-quinazolin-3-yl)-piperidine-2,6-dione in a cycling therapy that includes an administration period of at least 2 days and a rest period of at least 1 day. Other cycling therapy dosing regimens are described. Provided herein is also Compound 1 for use in methods for treating, preventing, managing and/or ameliorating lymphoma in a subject, while reducing an adverse effect associated with said treating, managing, and/or ameliorating, wherein the compound is 3-(5-amino-2-methyl-4-oxo-4H-quinazolin-3-yl)-piperidine-2,6-dione, or a pharmaceutically acceptable salt, solvate, hydrate, polymorph, stereoisomer, tautomer or racemic mixture thereof, and wherein the method comprises administering to a subject in need thereof an effective amount of said compound in a cycling therapy. Pharmaceutical compositions and dosing regimens for such treatment, prevention, and/or management are also provided herein.

2. BACKGROUND OF THE INVENTION

Lymphoma refers to cancers that originate in the lymphatic system. Lymphoma is characterized by malignant neoplasms of lymphocytes—B lymphocytes and T lymphocytes (i.e., B-cells and T-cells). Lymphoma generally starts in lymph nodes or collections of lymphatic tissue in organs including, but not limited to, the stomach or intestines. Lymphoma may involve the marrow and the blood in some cases. Lymphoma may spread from one site to other parts of the body.

The treatment of various forms of lymphomas are described, for example, in U.S. Pat. No. 7,468,363, the entirety of which is incorporated herein by reference. Such lymphomas include, but are not limited to, Hodgkin's lymphoma, non-Hodgkin's lymphoma, cutaneous B-cell lymphoma, activated B-cell lymphoma, diffuse large B-cell lymphoma (DLBCL), mantle cell lymphoma (MCL), follicular center lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-Cell lymphoma and mantle zone lymphoma and low grade follicular lymphoma.

Non-Hodgkin's lymphoma (NHL) is the fifth most common cancer for both men and women in the United States, with an estimated 63,190 new cases and 18,660 deaths in 2007. Jemal A, et al., *CA Cancer J Clin* 2007; 57(1):43-66. The probability of developing NHL increases with age and the incidence of NHL in the elderly has been steadily increasing in the past decade, causing concern with the aging trend of the US population. Id. Clarke C A, et al., *Cancer* 2002; 94(7):2015-2023.

Diffuse large B-cell lymphoma (DLBCL) accounts for approximately one-third of non-Hodgkin's lymphomas. While some DLBCL patients are cured with traditional chemotherapy, the remainder die from the disease. Anticancer drugs cause rapid and persistent depletion of lymphocytes, possibly by direct apoptosis induction in mature T and B cells. See K. Stahnke. et al., *Blood* 2001, 98:3066-3073. Absolute lymphocyte count (ALC) has been shown to be a prognostic factor in follicular non-Hodgkin's lymphoma and recent results have suggested that ALC at diagnosis is an important prognostic factor in diffuse large B-cell lymphoma. See D. Kim et al., *Journal of Clinical Oncology*, 2007 ASCO Annual Meeting Proceedings Part I. Vol 25, No. 18S (June 20 Supplement), 2007: 8082.

There exists a significant need for safe and effective methods of treating, preventing and managing cancer, including lymphoma such as diffuse large B-cell lymphoma (DLBCL).

3. SUMMARY

Provided herein are methods of treating and preventing cancer, including lymphoma such as DLBCL, and preventing or reducing adverse effects associated with treating, preventing, managing, or ameliorating of such diseases by administering 3-(5-amino-2-methyl-4-oxo-4H-quinazolin-3-yl)-piperidine-2,6-dione

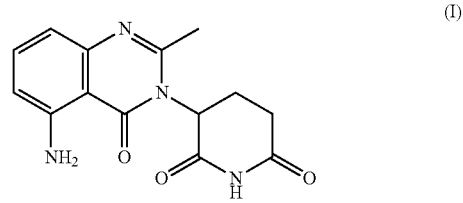 [SMILES: Cc1nc2cccc(N)c2c(=O)n1C1CCC(=O)NC1=O]

or a pharmaceutically acceptable salt, solvate, hydrate, stereoisomer, tautomer or racemic mixtures thereof (Compound 1) in a cycling therapy that includes an administration period of 5 or more days and a rest period of one or more days. In one embodiment, DLBCL is relapsed or refractory.

Also provided herein is Compound 1 for use in a method of treating and preventing cancer, including lymphoma such as DLBCL, and preventing or reducing adverse effects associated with treating, preventing, managing, or ameliorating of such diseases.

Provided herein are methods of treating lymphoma, including DLBCL, or a condition associated therewith, while reducing an adverse effect associated with such treatment by administering to a subject in need thereof an effective amount of Compound 1, wherein the compound is administered to the subject in a cycling therapy that includes an administration period of 5 or more days and a rest period of one or more days. Also provided herein is Compound 1 for use in said methods. Provided herein are methods of preventing lymphoma, including DLBCL, or a condition associated therewith, while reducing an adverse effect associated with such method by administering to a subject in need thereof an effective amount of Compound 1,wherein the compound is administered to the subject in a cycling therapy that includes an administration period of 5 or more days and a rest period of one or more days. Also provided herein is Compound 1 for use in said methods. Provided herein are methods of managing lymphoma, including DLBCL, or a condition associated therewith, while reducing an adverse effect associated with such method by administering to a subject in need thereof an effective amount of Compound 1, wherein the compound is administered to the subject in a cycling therapy that includes an administration period of 5 or more days and a rest period of one or more days. Also provided herein is Compound 1 for use in said methods. Provided herein are methods of ameliorating lymphoma, including DLBCL, or a condition associated therewith, while reducing an adverse effect associated with such method by administering to a subject in need thereof an effective amount of Compound 1, wherein the compound is administered to the subject in a cycling therapy that includes an administration period of 5 or more days and a rest period of one or more days. Also provided herein is Compound 1 for use in said methods.

Also provided herein are methods of treating, preventing, managing, and/or ameliorating lymphoma, including DLBCL, or a condition associated therewith, while reducing an adverse effect associated with such treatment, prevention, management, or amelioration by administering to a subject in need thereof an effective amount of Compound 1, wherein the compound is administered to the subject in a cycling therapy that includes an administration period of 5 or more days and a rest period of one or more days. In one embodiment, DLBCL is relapsed or refractory. Also provided herein is Compound 1 for use in said methods.

Also provided herein are methods of treating, preventing, managing, and/or ameliorating cancer, including lymphoma such as DLBCL, or a condition associated therewith, while reducing an adverse effect associated with such treatment, prevention, management, or amelioration by administering to a subject in need thereof an effective amount of Compound 1, wherein the compound is administered to the subject in a cycling therapy that includes (a) an administration period of 21 days followed by a rest period of 7 days, or (b) an administration period of 5 days followed by a rest period of 2 days. In one embodiment, DLBCL is relapsed or refractory. Also provided herein is Compound 1 for use in said methods.

Also provided herein are methods of treating, preventing, managing, and/or ameliorating DLBCL, or a condition associated therewith, while reducing an adverse effect associated with such treatment, prevention, management, or amelioration by administering to a subject in need thereof an effective amount of Compound 1, wherein the compound is administered to the subject in a cycling therapy that includes an administration period of 5 days followed by a rest period of 2 days. In one embodiment, DLBCL is relapsed or refractory. Also provided herein is Compound 1 for use in said methods.

Provided herein are methods of treating lymphoma, including DLBCL, or a condition associated therewith, while reducing an adverse effect associated with such treatment by administering to a subject in need thereof an effective amount of Compound 1, wherein the compound is administered to the subject in a cycling therapy that includes an administration period of 5 or more days and a rest period of one or more days. Provided herein are methods of preventing lymphoma, including DLBCL, or a condition associated therewith, while reducing an adverse effect associated with such method by administering to a subject in need thereof an effective amount of Compound 1, wherein the compound is administered to the subject in a cycling therapy that includes an administration period of 5 or more days and a rest period of one or more days. Also provided herein is Compound 1 for use in said methods. Provided herein are methods of managing lymphoma, including DLBCL, or a condition associated therewith, while reducing an adverse effect associated with such method by administering to a subject in need thereof an effective amount of Compound 1, wherein the compound is administered to the subject in a cycling therapy that includes an administration period of 5 or more days and a rest period of one or more days. Provided herein are methods of ameliorating lymphoma, including DLBCL, or a condition associated therewith, while reducing an adverse effect associated with such method by administering to a subject in need thereof an effective amount of Compound 1, wherein the compound is administered to the subject in a cycling therapy that includes an administration period of 5 or more days and a rest period of one or more days. Also provided herein is Compound 1 for use in said methods.

Also provided herein are methods of treating, preventing, managing, and/or ameliorating lymphoma, including DLBCL, or a condition associated therewith, while reducing an adverse effect associated with such treatment, prevention, management, or amelioration by administering to a subject in need thereof an effective amount of Compound 1, wherein the compound is administered to the subject in a cycling therapy that includes an administration period of 21 days followed by a rest period of 7 days. In one embodiment, DLBCL is relapsed or refractory. Also provided herein is Compound 1 for use in said methods.

In one embodiment, the cycling therapy includes an administration period of 5 days followed by a rest period of 2 days.

In one embodiment the cycling therapy includes an extended administration period followed by a rest period of one or more days.

In one embodiment the cycling therapy includes 21 days administration period followed by a rest period of 7 days.

In certain embodiment, provided herein are methods for reducing an adverse effect associated with treatment, prevention, management, or amelioration by administering to a subject in need thereof an effective amount of Compound 1, wherein the compound is administered to the subject in a cycling therapy that includes an administration period of 5 days followed by a rest period of 2 days. Also provided herein is Compound 1 for use in said methods.

In certain embodiments, lymphoma is selected from Hodgkin's lymphoma, non-Hodgkin's lymphoma, AIDS-related lymphomas, anaplastic large-cell lymphoma, angioimmunoblastic lymphoma, blastic NK-cell lymphoma, Burkitt's lymphoma, Burkitt-like lymphoma, small non-cleaved cell lymphoma, enteropathy-type T-cell lymphoma, lymphoblastic lymphoma, marginal zone lymphoma, nasal T-cell lymphoma, pediatric lymphoma, primary central nervous system lymphoma, activated B-cell lymphoma, cutaneous B-cell lymphoma, diffuse large B-cell lymphoma (DLBCL), mantle cell lymphoma (MCL), follicular center lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-Cell lymphoma, treatment-related T-cell lymphomas, Waldenstrom's macroglobulinemia, and mantle zone lymphoma and low grade follicular lymphoma. In one embodiment, lymphoma is relapsed or refractory DLBCL.

In one embodiment, lymphoma is Hodgkin's lymphoma. In one embodiment, lymphoma is non-Hodgkin's lymphoma. In one embodiment, lymphoma is AIDS-related lymphomas. In one embodiment, lymphoma is anaplastic large-cell lymphoma. In one embodiment, lymphoma is angioimmunoblastic lymphoma. In one embodiment, lymphoma is blastic NK-cell lymphoma. In one embodiment, lymphoma is Burkitt's lymphoma. In one embodiment, lymphoma is Burkitt-like lymphoma. In one embodiment, lymphoma is small non-cleaved cell lymphoma. In one embodiment, lymphoma is enteropathy-type T-cell lymphoma. In one embodiment, lymphoma is lymphoblastic lymphoma. In one embodiment, lymphoma is marginal zone lymphoma. In one embodiment, lymphoma is nasal T-cell lymphoma. In one embodiment, lymphoma is pediatric lymphoma. In one embodiment, lymphoma is primary central nervous system lymphoma. In one embodiment, lymphoma is activated B-cell lymphoma. In one embodiment, lymphoma is cutaneous B-cell lymphoma. In one embodiment, lymphoma is diffuse large B-cell lymphoma (DLBCL). In one embodiment, lymphoma is mantle cell lymphoma (MCL). In one embodiment, lymphoma is follicular center lymphoma. In one embodiment, lymphoma is transformed lymphoma. In one embodiment, lymphoma is lymphocytic lymphoma of intermediate differentiation. In one embodiment, lymphoma is intermediate lymphocytic lymphoma (ILL). In one embodiment, lymphoma is diffuse poorly differentiated lymphocytic lymphoma (PDL). In one embodiment, lymphoma is centrocytic lymphoma. In one embodiment, lymphoma is diffuse small-cleaved cell lymphoma (DSCCL). In one embodiment, lymphoma is peripheral T-cell lymphomas (PTCL). In one embodiment, lymphoma is cutaneous T-Cell lymphoma. In one embodiment, lymphoma is treatment-related T-cell lymphomas. In one embodiment, lymphoma is Waldenstrom's macroglobulinemia. In one embodiment, lymphoma is mantle zone lymphoma. In one embodiment, lymphoma is low grade follicular lymphoma.

Also provided herein is Compound 1 for use in any of the methods provided herein.

Also provided herein are pharmaceutical compositions, single unit dosage forms, and kits suitable for use in treating, preventing, ameliorating and/or managing lymphoma or condition associated therewith while reducing an adverse effect associated with such treatment where such compositions include Compound 1 optionally in combination with one or more other therapeutic agents.

In some embodiments, provided herein are methods for the treatment or management of non-Hodgkin's lymphomas, including but not limited to, diffuse large B-cell lymphoma (DLBCL), using prognostic factors.

In certain embodiments, the lymphoma is of the activated B-cell phenotype in non-Hodgkin's lymphoma.

4. BRIEF DESCRIPTION OF THE FIGURES

FIG. 1 provides results of in vitro myeloid differentiation assay with 3-(5-amino-2-methyl-4-oxo-4H-quinazolin-3-yl)-piperidine-2,6-dione.

FIG. 2 demonstrates mitigation of severity of neutropenia in patients on 5/7 day schedule of 3-(5-amino-2-methyl-4-oxo-4H-quinazolin-3-yl)-piperidine-2,6-dione.

Figure 5:
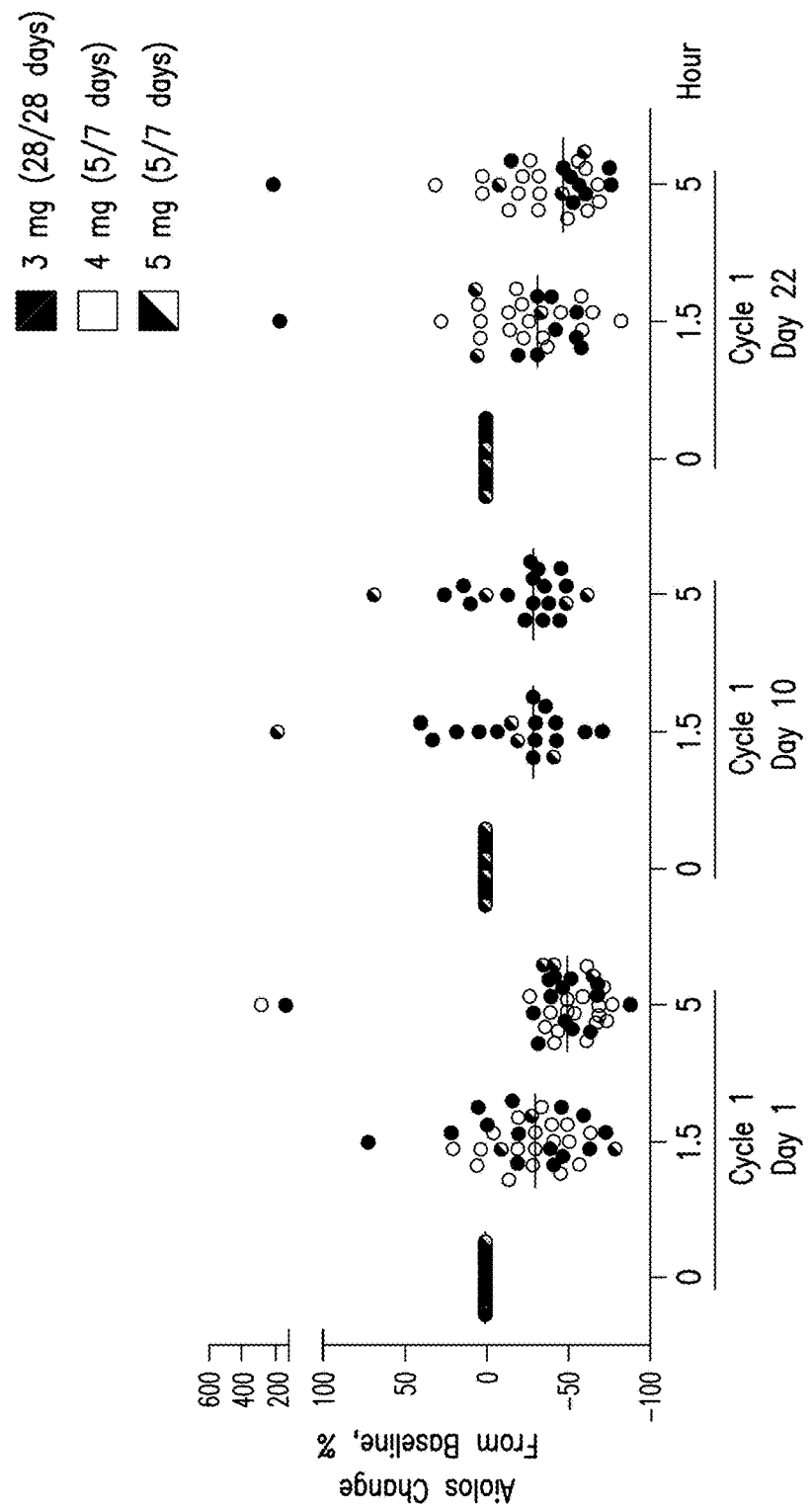

FIG. 5 illustrates the median change in Aiolos levels relative to baseline in peripheral T cells when measured 5 hours post-dosing 3-(5-amino-2-methyl-4-oxo-4H-quinazolin-3-yl)-piperidine-2,6-dione on cycle 1, days 1, 10, and 22.

Figure 6:
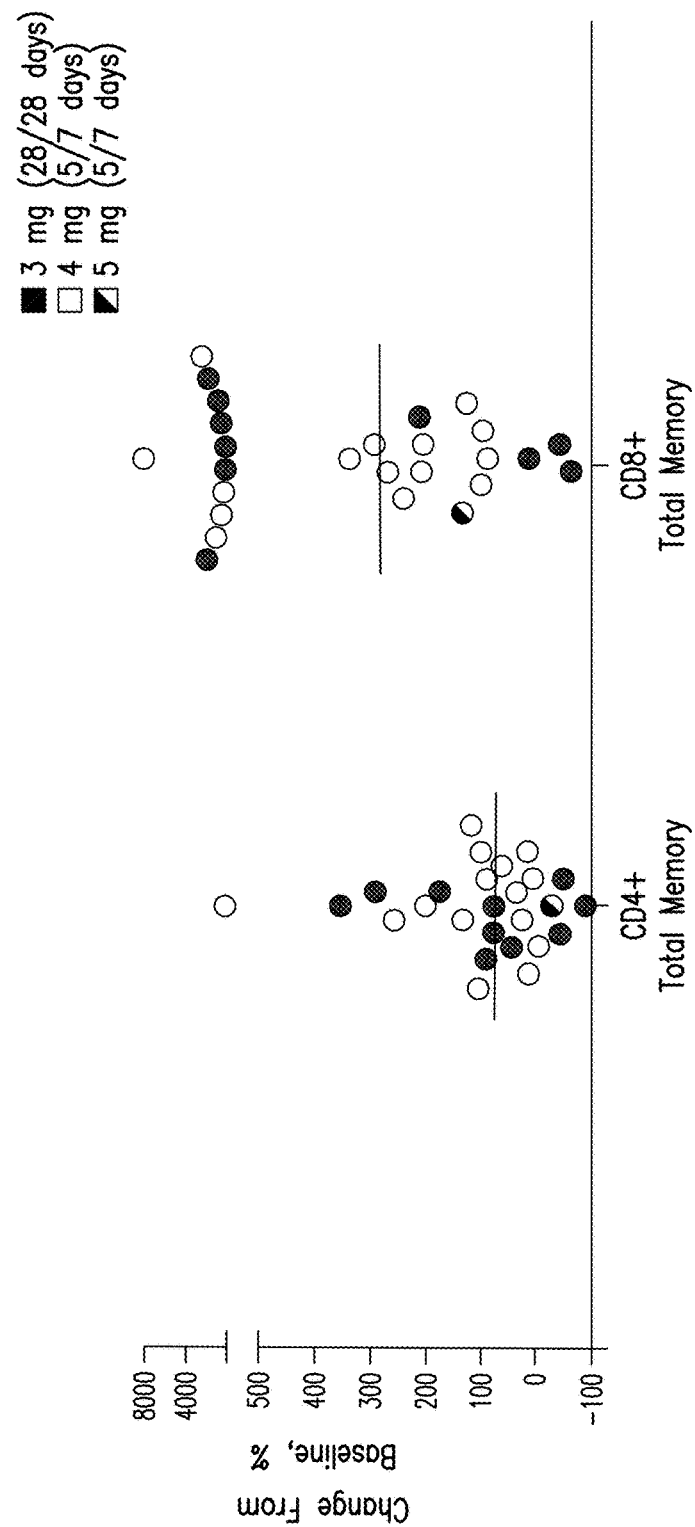

FIG. 6 illustrates the median increase from baseline in helper memory T cells and cytotoxic memory T cells on 5/7 d schedule with 3-(5-amino-2-methyl-4-oxo-4H-quinazolin-3-yl)-piperidine-2,6-dione.

Figure 7A:
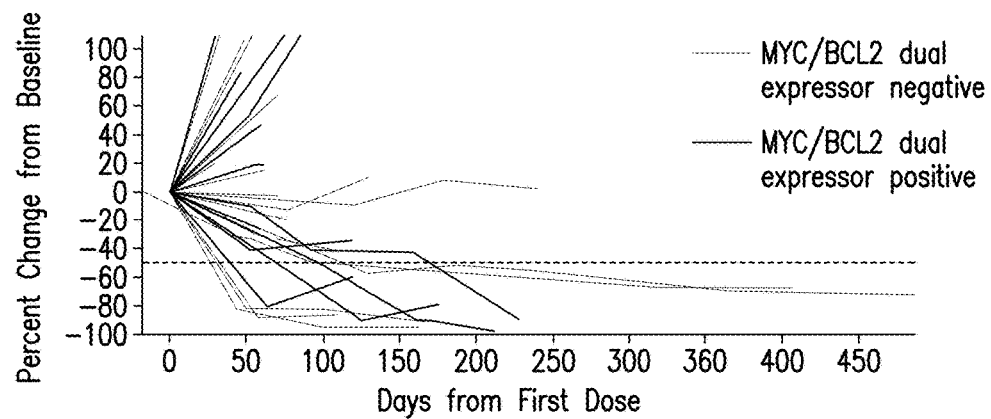

FIG. 7A demonstrates responses to 3-(5-amino-2-methyl-4-oxo-4H-quinazolin-3-yl)-piperidine-2,6-dione as determined by 50% reduction in tumor size were observed in both MYC/BCL2-positive and -negative disease.

Figure 7B:
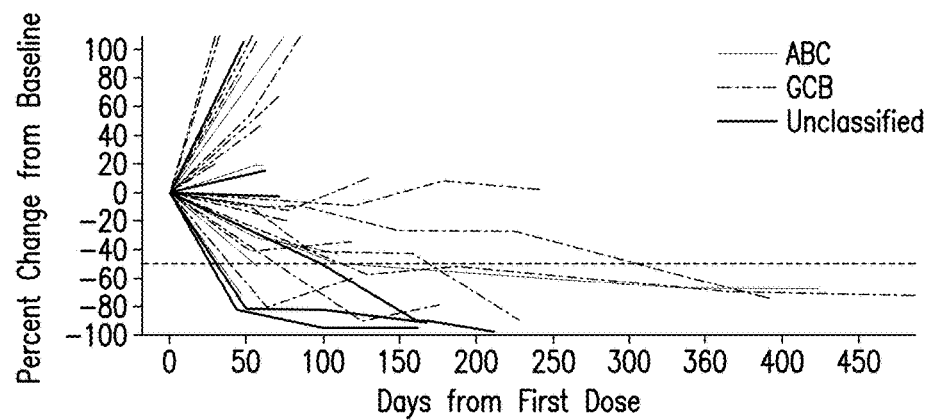

FIG. 7B demonstrates responses to 3-(5-amino-2-methyl-4-oxo-4H-quinazolin-3-yl)-piperidine-2,6-dione as determined by 50% reduction in tumor size were observed in ABC, GCB, and unclassified cell of origin.

5. DETAILED DESCRIPTION OF THE INVENTION

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

5.1 Definitions

To facilitate understanding of the disclosure set forth herein, a number of terms are defined below.

The term "subject" or "patient" refers to an animal, including, but not limited to, a mammal, including a primate (e.g., human), cow, sheep, goat, horse, dog, cat, rabbit, rat, or mouse. The terms "subject" and "patient" are used interchangeably herein in reference, for example, to a mammalian subject, such as a human subject.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a patient with such a disease or disorder. In some embodiments, the terms refer to the administration of a compound provided herein, with or without other additional active agent, after the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of diseases or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a patient derives from a prophylactic and/or therapeutic agent do not result in a cure of the disease or disorder. In this regard, the term "managing" encompasses treating a patient who had suffered from the particular disease in an attempt to prevent or minimize the recurrence of the disease, or lengthening the time during which the remains in remission.

The term "adverse effect" is used according to its ordinary and common meaning in the art and as used herein can refer to a specific condition associated with treatment, prevention, management, or amelioration of a disease described herein resulting from treatment with a compound or composition described herein. One such adverse effect is the onset of neutropenia. Neutropenia can result from damage to bone marrow, and refers to any condition causing inhibition, elimination, or disruption (directly or indirectly) of neutrophil production and/or maturation.

An improvement in the disease can be characterized as a complete or partial response. "Complete response" refers to an absence of clinically detectable disease with normalization of any previously abnormal radiographic studies, bone marrow, and cerebrospinal fluid (CSF) or abnormal monoclonal protein measurements. "Partial response" refers to at least about a 10%, 20%, 30%, 40%, 50%, 60%, 70%, 80%, or 90% decrease in all measurable tumor burden (i.e., the number of malignant cells present in the subject, or the measured bulk of tumor masses or the quantity of abnormal monoclonal protein) in the absence of new lesions. The term "treatment" contemplates both a complete and a partial response.

The term "refractory or resistant" refers to a circumstance where a subject or a mammal, even after intensive treatment, has residual cancer cells in his body.

The term "drug resistance" refers to the condition when a disease does not respond to the treatment of a drug or drugs. Drug resistance can be either intrinsic, which means the disease has never been responsive to the drug or drugs, or it can be acquired, which means the disease ceases responding to a drug or drugs that the disease had previously responded to. In certain embodiments, drug resistance is intrinsic. In certain embodiments, the drug resistance is acquired.

The term "relapsed" refers to a situation where a subject or a mammal, which has had a remission of cancer after therapy has a return of cancer cells.

An "cycling therapy" refers to a regimen or therapy that includes an administration period as described herein and a rest period as described herein.

The term "administration period" as used herein refers to a period of time a subject is continuously or actively administered a compound or composition described herein.

The term "rest period" as used herein refers to a period of time, often following an administration period, where a subject is not administered a compound or composition described herein (e.g. discontinuation of treatment). In certain embodiments, a "rest period" refers to a period of time where a single agent is not administered to a subject or treatment using a particular compound is discontinued. In such embodiments, a second therapeutic agent (e.g., a different agent than the compound or composition administered in the previous administration period) can be administered to the subject.

The term "QD" refers to a once daily dose administration.

The terms "determining", "measuring", "evaluating", "assessing" and "assaying" as used herein generally refer to any form of measurement, and include determining if an element is present or not. These terms include both quantitative and/or qualitative determinations. Assessing may be relative or absolute. "Assessing the presence of" can include determining the amount of something present, as well as determining whether it is present or absent.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein and unless otherwise indicated, the term "pharmaceutically acceptable salt" includes, but is not limited to, a salt of an acidic group that can be present in the compounds provided herein. Under certain acidic conditions, the compound can form a wide variety of salts with various inorganic and organic acids. The acids that can be used to prepare pharmaceutically acceptable salts of such basic compounds are those that form salts such as pharmacologically acceptable anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, methanesulfonate (mesylate), methylsulfate, muscate, napsylate, nitrate, pantothenate, phosphate/diphosphate, polygalacturonate, salicylate, stearate, succinate, sulfate, tannate, tartrate, teoclate, triethiodide, and pamoate.

As used herein and unless otherwise indicated, the term "hydrate" means a compound provided herein or a salt thereof, further including a stoichiometric or non-stoichiometric amount of water bound by non-covalent intermolecular forces. The hydrates can be crystalline or non-crystalline.

As used herein and unless otherwise indicated, the term "solvate" means a solvate formed from the association of one or more solvent molecules to compound provided herein. The term "solvate" includes hydrates (e.g., monohydrate, dihydrate, trihydrate, tetrahydrate, and the like). The solvates can be crystalline or non-crystalline.

As used herein, and unless otherwise specified, the term "stereoisomer" encompasses all enantiomerically/stereomerically pure and enantiomerically/stereomerically enriched compounds provided herein.

As used herein, and unless otherwise indicated, the term "stereomerically pure" or "enantiomerically pure" means that a compound includes one stereoisomer and is substantially free of its counter stereoisomer or enantiomer. For example, a compound is stereomerically or enantiomerically pure when the compound contains 80%, 90%, or 95% or more of one stereoisomer and 20%, 10%, or 5% or less of the counter stereoisomer. In certain cases, a compound provided herein is considered optically active or stereomerically/enantiomerically pure (i.e., substantially the R-form or substantially the S-form) with respect to a chiral center when the compound is about 80% ee (enantiomeric excess) or greater, preferably, equal to or greater than 90% ee with respect to a particular chiral center, and more preferably 95% ee with respect to a particular chiral center.

As used herein, and unless otherwise indicated, the term "stereomerically enriched" or "enantiomerically enriched" encompasses racemic mixtures as well as other mixtures of stereoisomers of compounds provided herein (e.g., R/S=30/70, 35/65, 40/60, 45/55, 55/45, 60/40, 65/35 and 70/30).

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition; Lippincott Williams & Wilkins: Philadelphia, Pa., 2005; Handbook of Pharmaceutical Excipients, 5th Edition; Rowe et al., Eds., The Pharmaceutical Press and the American Pharmaceutical Association: 2005; and *Handbook of Pharmaceutical Additives,* 3rd Edition; Ash and Ash Eds., Gower Publishing Company: 2007; *Pharmaceutical Preformulation and Formulation,* Gibson Ed., CRC Press LLC: Boca Raton, Fla., 2004).

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

5.2 Compound

The compound suitable for use in the methods provided herein is 3-(5-amino-2-methyl-4-oxo-4H-quinazolin-3-yl)-piperidine-2,6-dione, having the structure of Formula I:

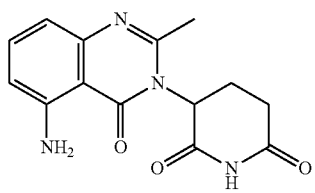

(I)

or an enantiomer or a mixture of enantiomers thereof; or a pharmaceutically acceptable salt, solvate, hydrate, co-crystal, clathrate, or polymorph thereof (Compound 1).

Compound 1 can be prepared according to the methods described in the Examples provided herein or as described in U.S. Pat. No. 7,635,700, the disclosure of which is incorporated herein by reference in its entirety. The compound can be also synthesized according to other methods apparent to those of skill in the art based upon the teaching herein.

In certain embodiments, Compound 1 is a solid. In certain embodiments, Compound 1 is hydrated. In certain embodiments, Compound 1 is solvated. In certain embodiments, Compound 1 is anhydrous. In certain embodiments, Compound 1 is nonhygroscopic.

In certain embodiments, Compound 1 is amorphous. In certain embodiments, Compound 1 is crystalline. In certain embodiments, the solid Compound 1 is in a crystalline form described in U.S. Pat. No. 8,802,685, which is incorporated herein by reference in its entirety.

The solid forms of Compound 1 can be prepared according to the methods described in the disclosure of U.S. Pat. No. 8,802,685. The solid forms can be also prepared according to other methods apparent to those of skill in the art.

In certain embodiments, Compound 1 is a hydrochloride salt of 3-(5-amino-2-methyl-4-oxo-4H-quinazolin-3-yl)-piperidine-2,6-dione, or an enantiomer or a mixture of enantiomers thereof; or a pharmaceutically acceptable solvate, hydrate, co-crystal, clathrate, or polymorph thereof. In certain embodiments, the hydrochloride salt is a solid. In certain embodiments, the hydrochloride salt is anhydrous. In certain embodiments, the hydrochloride salt is nonhygroscopic. In certain embodiments, the hydrochloride salt is amorphous. In certain embodiments, the hydrochloride salt is crystalline. In certain embodiments, the hydrochloride salt is in crystalline Form A.

The hydrochloride salt of Compound 1 and solid forms thereof can be prepared according to the methods described in the disclosure of U.S. Pat. No. 8,802,685. The hydrochloride salt the solid forms thereof can be also prepared according to other methods apparent to those of skill in the art.

Compound 1 provided herein contains one chiral center, and can exist as a mixture of enantiomers, e.g., a racemic mixture. This disclosure encompasses the use of stereomerically pure forms of such a compound, as well as the use of mixtures of those forms. For example, mixtures comprising equal or unequal amounts of the enantiomers of Compound 1 provided herein may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of the structure.

5.3 Cycling Therapy

The compounds described herein can be cyclically administered to a patient in need thereof in connection with the methods described herein. Cycling therapy involves the administration of an active agent for a period of time (an administration period), followed by a rest for a period of time (a rest period), and repeating this sequential administration.

Cycling therapy can reduce the development of resistance to one or more of the therapies, avoid or reduce the side effects of one of the therapies, and/or improve the efficacy of the treatment. Thus in certain instances, the cycling therapies described herein reduce adverse effects associated with administration of a compound or composition described herein (e.g., Compound 1 or a pharmaceutically acceptable salt, solvate, hydrate, stereoisomer, tautomer or racemic mixtures thereof).

In another aspect, the cycling therapy includes an administration period of 5 days followed by a 2 day rest period. In still another aspect, the cycling therapy includes an extended administration period followed by a 7 day rest period. An "extended administration period" as used herein refers to continual daily administration (e.g., QD) of Compound 1 for 7 or more days. In certain embodiments, an extended administration period includes continual daily administration of Compound 1 for 7, 8, 9, 10, 11, 12, 13, 14, 15, 16, 17, 18, 19, 20, or 21 days. In certain embodiments, an extended administration period includes continual daily administration of Compound 1 for 10, 11, 12, 13, 14, 15, 16, 17, 18, 19, 20, or 21 days. In one embodiment, the continual administration is for 7 days. In one embodiment, the continual administration is for 8 days. In one embodiment, the continual administration is for 9 days. In one embodiment, the continual administration is for 10 days. In one embodiment, the continual administration is for 11 days. In one embodiment, the continual administration is for 12 days. In one embodiment, the continual administration is for 13 days. In one embodiment, the continual administration is for 14 days. In one embodiment, the continual administration is for 15 days. In one embodiment, the continual administration is for 16 days. In one embodiment, the continual administration is for 17 days. In one embodiment, the continual administration is for 18 days. In one embodiment, the continual administration is for 19 days. In one embodiment, the continual administration is for 20 days. In one embodiment, the continual administration is for 21 days.

In another embodiment the cycling therapy includes an administration period of at least 7 continual days of administration. The administration period can be 21 days, where the administration period is repeated for at least 1 more cycles as described herein.

Cycling therapies described herein can be repeated for at least 2, 3, 4, 5, 6, 7, 8, or more cycles. In certain instances a cycling therapy as described herein includes from one to about 24 cycles, from about two to about 16 cycles, or from about two to about four cycles. In certain instances, the cycling therapy is not limited to the number of cycles, and the therapy is continued until diease progression. Cycles, can in certain instances, include varying the duration of administration periods and/or rest periods described herein.

In one aspect is a cycling therapy that includes administering Compound 1 as described herein in an administration period of 5 days followed by a 2 day rest period (e.g., a 5/7 cycling therapy). In one embodiment, the 5/7 cycling therapy is repeated from about 2 to about 16 cycles. In one embodiment, the 5/7 cycling therapy is repeated 2, 3, or 4 cycles. The dosage amount of Compound 1 in the 5/7 cycling therapy is as described herein. In one embodiment the 5/7 cycling therapy includes administering Compound 1 at a dosage amount of about 0.1 mg to about 20 mg, from about 0.1 mg to about 15 mg, from about 0.1 mg to about 10 mg, from about 1 mg to about 7 mg, from about 1 mg to about 5 mg, from about 1 mg to about 4 mg, or from about 1 mg to about 3 mg.

In one embodiment the 5/7 cycling therapy includes administering Compound 1 at a dosage amount of about 1 mg, 2 mg, 3 mg, 4 mg or 5 mg.

In certain embodiments, the amount of compound administered in the 5/7 cycling therapy is greater than an amount administered in an extended administration period described herein. Without being bound by any particular theory, a higher dosage administration may be more tolerable to a patient and result in greater efficacy over the shortened administration period.

In other embodiments, the amount of the compound administered in a 5/7 cycling therapy described herein is less than an amount administered in an extended administration period described herein. Such lowered administration can be performed over any number of cycles described herein and in particular over a number of cycles greater than 1, 3, 5, 7, or 10 cycles. In certain embodiments, the lower amount of administered compound allows for decreased observation of development of resistance to the compound.

In another aspect is cycling therapy that includes administering Compound 1 as described herein in an extended administration period as described herein followed by a 7 day rest period. In one embodiment the extended administration period includes administering Compound 1 as described herein daily over 21 continual days. In one embodiment the cycling therapy includes an extended administration period is repeated consecutively over 3, 4, 5, 6, 7, 8, 9, or more cycles.

In one embodiment, a cycling therapy that includes an extended administration period described herein includes administration of Compound 1 daily at a dosage amount of about 0.1 mg to about 20 mg, from about 0.1 mg to about 15 mg, from about 0.1 mg to about 10 mg, from about 1 mg to about 7 mg, from about 1 mg to about 5 mg, from about 1 mg to about 4 mg, or from about 1 mg to about 3 mg.

In one embodiment, the amount of compound administered in a cycling therapy that includes an extended administration period described herein is 3 or 4 mg. In one embodiment, the amount of compound administered in a cycling therapy that includes an extended administration period described herein is from about 3 mg to about 4 mg.

In yet another aspect is a cycling therapy that includes one or more of the cycling therapies described herein. Thus in one embodiment, a cycling therapy includes at least one 5/7 cycle as set forth above and at least one cycling therapy that includes an extended administration period. Compound 1 can be administered at the same amount for all administration periods in such cycling therapies and can be administered as described herein. Alternatively, in one embodiment, the compound is administered at different doses between the administration periods (e.g., a 5 day administration period and an extended administration period described herein). In one such embodiment, Compound 1 is administered at an amount lower in a second administration period than a first administration period as described herein. Compound 1 can be administered according to the dosages and dosage amounts described herein.

Cyclic therapies that include administration periods of varying lengths as set forth above can be administered in any order and independently in any number of cycles described herein. Thus, in one embodiment is a cycling therapy of Compound 1 that includes at least 1, 2, 3, 4, 5, 6 or more 5/7 cycling therapies as described herein and 1, 2, 3, 4, 5, 6 or more cycling therapies that include an extended administration period as described herein, where the two therapies can be administered in any combination (e.g., two 5/7 cycling therapies followed by 1 cycling therapy that includes an extended administration period.)

In some embodiments, certain doses of a compound or composition described herein can reduce or block differentiation of a population of cells as described herein into neutrophils. In certain embodiments, introduction of a rest period in the cycle allows for (or increases) maturation of neutrophils in the patient.

Provided herein in one embodiment is a method of treating, preventing, managing, and/or ameliorating cancer while reducing an adverse effect described herein associated with such treatment, prevention, management, or amelioration by administering to a subject in need thereof an effective amount of Compound 1 where the compound is administered to the subject in a cycling therapy that includes (a) an administration period of 5 days followed by a rest period of 2 days or (b) an extended administration period of 21 days as described herein followed by a rest period of 7 days, and where the cycling therapy is administered to the patient for a period of at least 1 cycle.

5.4 Dosages

The dose of Compound 1 to be administered to a patient can be subject to the judgment of a health-care practitioner. Doses of Compound 1 vary depending on factors such as: specific indication to be treated, prevented, or managed; age and condition of a patient; and amount of second active agent used, if any. In general, Compound 1 can be administered one to four or more times a day in a dose of about 0.005 mg/kg of a patient's body weight to about 10 mg/kg of a patient's body weight in a patient, but the above dosage may be properly varied depending on the age, body weight and medical condition of the patient and the type of administration. In one embodiment, the dose is about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight or about 0.25 mg/kg of a patient's body weight to about 0.5 mg/kg of a patient's body weight. In one embodiment, the dose is about 0.01 mg/kg of a patient's body weight to about 5 mg/kg of a patient's body weight. In one embodiment, the dose is about 0.05 mg/kg of a patient's body weight to about 1 mg/kg of a patient's body weight. In one embodiment, the dose is about, 0.1 mg/kg of a patient's body weight to about 0.75 mg/kg of a patient's body weight. In one embodiment, the dose is about 0.25 mg/kg of a patient's body weight to about 0.5 mg/kg of a patient's body weight.

In one embodiment, one dose is given per day. In any given case, the amount of Compound 1 administered will depend on such factors as the solubility of the active component, the formulation used, the route of administration, and patient tolerance. As a result, in certain embodiments, two or more doses of a compound or composition as described herein can be administered to a subject described herein. In one embodiment, application of a topical concentration provides intracellular exposures or concentrations of about 0.01-10μM.

In certain embodiments, Compound 1 is used in an amount from about 0.1 mg to about 50 mg per day, and can be adjusted in a conventional fashion (e.g., the same amount administered each day of the treatment, prevention or management period), in cycles (e.g., one week on, one week off, a set number of days on, a set number of days off), or in an amount that increases or decreases over the course of treatment, prevention, or management. In other embodiments, the dose can be from about 0.1 mg to about 30 mg, from about 0.1 mg to about 25 mg, from about 0.1 mg to about 20 mg, from about 0.1 mg to about 15 mg, from about 0.1 mg to about 10 mg, from about 0.1 mg to about 7 mg, from about 1 mg to about 15 mg, from about 1 mg to about 10 mg, or from about 1 mg to about 7 mg. In other embodiments, the dose can be from about 1 mg to about 5 mg, from about 1 mg to about 4 mg, from about 2 mg to about 6 mg, from about 2 mg to about 5 mg, or from about 2 mg to about 4 mg.

In other embodiments, the dose can be from about 0.1 mg to about 30 mg. In other embodiments, the dose can be from about 0.1 mg to about 25 mg. In other embodiments, the dose can be from about 0.1 mg to about 20 mg. In other embodiments, the dose can be from about 0.1 mg to about 15 mg. In other embodiments, the dose can be from about 0.1 mg to about 10 mg. In other embodiments, the dose can be from about 0.1 mg to about 7 mg. In other embodiments, the dose can be from about 1 mg to about 15 mg. In other embodiments, the dose can be from about 1 mg to about 10 mg. In other embodiments, the dose can be from about 1 mg to about 7 mg. In other embodiments, the dose can be from about 1 mg to about 5 mg. In other embodiments, the dose can be from about 1 mg to about 4 mg. In other embodiments, the dose can be from about 2 mg to about 6 mg. In other embodiments, the dose can be from about 2 mg to about 5 mg. In other embodiments, the dose can be from about 2 mg to about 4 mg. In other embodiments, the dose can be from about 3 mg to about 7mg. In other embodiments, the dose can be from about 4 mg to about 7 mg. In other embodiments, the dose can be from about 3 mg to about 5 mg. In other embodiments, the dose can be from about 4 mg to about 5 mg. In other embodiments, the dose can be from about 5 mg to about 6 mg. In other embodiments, the dose can be from about 5 mg to about 7 mg. In other embodiments, the dose can be from about 3 mg to about 4 mg.

In particular embodiments, the dose is about 1, 2, 3, 4, 5, 6, 7, 8, 9, 10, 11, 12, 13, 14, 15, 16, 17, 18, 19 or 20 mg. In particular embodiments, the dose is about 1 mg. In particular embodiments, the dose is about 2 mg. In particular embodiments, the dose is about 3 mg. In particular embodiments, the dose is about 4 mg. In particular embodiments, the dose is about 5 mg. In particular embodiments, the dose is about 6 mg. In particular embodiments, the dose is about 7 mg. In particular embodiments, the dose is about 8 mg. In particular embodiments, the dose is about 9 mg. In particular embodiments, the dose is about 10 mg. In particular embodiments, the dose is about 11 mg. In particular embodiments, the dose is about 12 mg. In particular embodiments, the dose is about 13 mg. In particular embodiments, the dose is about 14 mg. In particular embodiments, the dose is about 15 mg. In particular embodiments, the dose is about 16.In particular embodiments, the dose is about 17 mg. In particular embodiments, the dose is about 18 mg. In particular embodiments, the dose is about 19 mg. In particular embodiments, the dose is about 20 mg. In other particular embodiments, the dose is about 2, 3, 4, or 5 mg. In another embodiment, the dose is about 3, 4 or 5 mg. As described herein in certain instances it can be beneficial to modulate the dosage over the treatment time to maximize effectiveness. Thus, in certain embodiments, a dose given in a first administration period is followed by a decreased dose provided in a second administration period. In certain embodiments the dose provided in a second or subsequent administration period is 10%, 20%, 25%, 30%, 40%, or 50% lower than the dose provided in a first administration period. In another embodiment, the dosage is varied within the administration period itself according to the amounts and dosages described herein. All doses described herein are equally applicable to contacting with a cell ex-vivo as described herein.

In certain embodiments, the dosage amount is determined by the cycling therapy used during treatment of the disease or disorder. In one embodiment, the amount of Compound 1 administered to a patient in need thereof is greater (e.g., about or greater than 1 mg) when the administration period is shorter.

In another embodiment, the amount of Compound 1 administered to a patient in need thereof is greater (e.g. about or greater than 1 mg) when the administration period is longer (e.g., an extended administration period as described herein).

In yet another embodiment, the amount of Compound 1 administered to a patient in need thereof is lower (e.g., less than about 1 mg) when the administration period is shorter.

In still another embodiment, the amount of Compound 1 administered to a patient in need thereof is lower (e.g., less than about 1 mg) when the administration period is longer (e.g., an extended administration period as described herein).

5.5 Methods of Treatment, Prevention and Management

In one embodiment, provided herein is a method of treating and preventing cancer while reducing an adverse effect associated with such treatment, prevention, management, or amelioration, by administering to a patient a compound provided herein, e.g., Compound 1, or an enantiomer or a mixture of enantiomers thereof, or a pharmaceutically acceptable salt, solvate, hydrate, co-crystal, clathrate, or polymorph thereof in a cycling therapy that includes an administration period of 5 days followed by a 2 day rest period or an administration period of 21 days followed by a 7 day rest period. In one embodiment, provided herein is the Compound 1, or an enantiomer or a mixture of enantiomers thereof, or a pharmaceutically acceptable salt, solvate, hydrate, co-crystal, clathrate, or polymorph thereof for use in a method of treating and preventing cancer while reducing an adverse effect associated with such treatment, prevention, management, or amelioration, by administering the Compound to a patient, e.g. in a cycling therapy that includes an administration period of 5 days followed by a 2 day rest period or an administration period of 21 days followed by a 7 day rest period.

As used herein, the term "cancer" includes, but is not limited to, solid tumors and blood born tumors. The term "cancer" refers to disease of skin tissues, organs, blood, and vessels, including, but not limited to, cancers of the bladder, bone, blood, brain, breast, cervix, chest, colon, endrometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant giolma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma.

In certain embodiments, the cancer is a solid tumor. In certain embodiments, the solid tumor is metastatic. In certain embodiments, the solid tumor is drug-resistant. In certain embodiments, the solid tumor is hepatocellular carcinoma, prostate cancer, ovarian cancer, or glioblastoma.

In certain embodiments, the cancer is a blood borne tumor. In certain embodiments, the blood borne tumor is metastatic. In certain embodiments, the blood borne tumor is drug resistant. In certain embodiments, the cancer is myeloma or lymphoma.

In another embodiment, provided herein are methods of treating, preventing or managing lymphoma, while reducing an adverse effect associated with such treatment, prevention, management, or amelioration, by administering to a patient a compound provided herein, e.g., Compound 1, or an enantiomer or a mixture of enantiomers thereof, or a pharmaceutically acceptable salt, solvate, hydrate, co-crystal, clathrate, or polymorph thereof, in a cycling therapy that includes an administration period of 5 days followed by a 2 day rest period or an administration period of 21 days followed by a 7 day rest period. In certain embodiments, lymphoma is selected from Hodgkin's lymphoma, non-Hodgkin's lymphoma, AIDS-related lymphomas, anaplastic large-cell lymphoma, angioimmunoblastic lymphoma, blastic NK-cell lymphoma, Burkitt's lymphoma, Burkitt-like lymphoma, small non-cleaved cell lymphoma, enteropathy-type T-cell lymphoma, lymphoblastic lymphoma, marginal zone lymphoma, nasal T-cell lymphoma, pediatric lymphoma, primary central nervous system lymphoma, activated B-cell lymphoma, cutaneous B-cell lymphoma, diffuse large B-cell lymphoma (DLBCL), mantle cell lymphoma (MCL), follicular center lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-Cell lymphoma, treatment-related T-cell lymphomas, Waldenstrom's macroglobulinemia, and mantle zone lymphoma and low grade follicular lymphoma.

In another embodiment, provided herein are methods of treating or managing non-Hodgkin's lymphoma, while reducing an adverse effect associated with such treatment, prevention, management, or amelioration, by administering to a patient a compound provided herein in a cycling therapy that includes an administration period of 5 days followed by a 2 day rest period or an administration period of 21 days followed by a 7 day rest period.

In some embodiments, provided herein are methods for the treatment or management of non-Hodgkin's lymphoma (NHL), including but not limited to, diffuse large B-cell lymphoma (DLBCL), while reducing an adverse effect associated with such treatment, prevention, management, or amelioration, by administering to a patient a compound provided herein in a cycling therapy that includes an administration period of 5 days followed by a 2 day rest period or an administration period of 21 days followed by a 7 day rest period. In some embodiments, DLBCL is refractory or relapsed.

In one embodiment, the diffuse large B-cell lymphoma is of the activated B-cell (ABC) phenotype.

In one embodiment, the diffuse large B-cell lymphoma is of the germinal center B-cell (GCB) phenotype.

In one embodiment, the diffuse large B-cell lymphoma is of unclassified cell of origin.

In some embodiments, provided herein are methods for the treatment or management of mantle cell lymphoma (MCL), while reducing an adverse effect associated with such treatment, prevention, management, or amelioration, by administering to a patient a compound provided herein in a cycling therapy that includes an administration period of 5 days followed by a 2 day rest period or an administration period of 21 days followed by a 7 day rest period.

Also provided herein are methods of treating patients who have been previously treated for the condition at issue but are non-responsive to standard therapies, as well as those who have not previously been treated. The invention also encompasses methods of treating patients regardless of patient's age, although some diseases or disorders are more common in certain age groups. The invention further encompasses methods of treating patients who have undergone surgery in an attempt to treat the disease or condition at issue, as well as those who have not. Because patients with lymphoma have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with lymphoma.

In certain embodiments, the patient to be treated with one of the methods provided herein has not been treated with anticancer therapy prior to the administration of Compound 1. In certain embodiments, the patient to be treated with one of the methods provided herein has been treated with anticancer therapy prior to the administration of Compound 1. In certain embodiments, the patient to be treated with one of the methods provided herein has developed drug resistance to the anticancer therapy.

The methods provided herein encompass treating a patient regardless of patient's age, although some diseases or disorders are more common in certain age groups. Further provided herein is a method for treating a patient who has undergone surgery in an attempt to treat the disease or condition at issue, as well in one who has not.

Depending on the disease to be treated and the subject's condition, Compound 1 may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. Compound 1 may be formulated, alone or together, in suitable dosage unit with pharmaceutically acceptable excipients, carriers, adjuvants and vehicles, appropriate for each route of administration.

In one embodiment, Compound 1 is administered orally. In another embodiment, Compound 1 is administered parenterally. In yet another embodiment, Compound 1 is administered intravenously.

Compound 1 can be delivered as a single dose such as, e.g., a single bolus injection, or oral tablets or pills; or over time, such as, e.g., continuous infusion over time or divided bolus doses over time. The compound can be administered repeatedly if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MM scan and other commonly accepted evaluation modalities.

5.5.1 Combination Therapy With a Second Active Agent

Compound 1 can also be combined or used in combination with other therapeutic agents useful in the treatment and/or prevention of cancer, including lymphoma described herein.

In one embodiment, provided herein is a method of treating, preventing, or managing lymphoma, comprising administering to a patient Compound 1 in combination with one or more second active agents, and optionally in combination with radiation therapy, blood transfusions, or surgery. Examples of second active agents are disclosed herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of Compound land one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

The route of administration of Compound 1 is independent of the route of administration of a second therapy. In one embodiment, Compound 1 is administered orally. In another embodiment, Compound 1 is administered intravenously. Thus, in accordance with these embodiments, Compound 1 is administered orally, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, Compound 1 and a second therapy are administered by the same mode of administration, orally or by IV. In another embodiment, Compound 1 is administered by one mode of administration, e.g., by IV, whereas the second agent (an anticancer agent) is administered by another mode of administration, e.g., orally.

In one embodiment, the second active agent is administered intravenously or subcutaneously and once or twice daily in an amount from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount of Compound 1 provided herein and any optional additional active agents concurrently administered to the patient.

In one embodiment, the second active agent is a large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. In certain embodiments, large molecule active agents are biological molecules, such as naturally occurring or artificially made proteins. Proteins that are particularly useful in this disclosure include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18;interferons, such as interferon alfa-2a, interferon alfa-2b, interferon alfa-nl, interferon alfa-n3, interferon beta-I a, and interferon gamma-I b; GM-CF and GM-CSF; and EPO.

Particular proteins that can be used in the methods and compositions of the disclosure include, but are not limited to: filgrastim, which is sold in the United States under the trade name NEUPOGEN® (Amgen, Thousand Oaks, Calif.); sargramostim, which is sold in the United States under the trade name LEUKINE® (Immunex, Seattle, Wash.); and recombinant EPO, which is sold in the United States under the trade name EPGEN® (Amgen, Thousand Oaks, Calif.).

Inhibitors of ActRII receptors or activin-ActRII inhibitors may be used in the methods and compositions provided herein. ActRII receptors include ActRIIA inhibitors and ActRIIB inhibitors. Inhibitors of ActRII receptors can be polypeptides comprising activin-binding domains of ActRII. In certain embodiments, the activin-binding domain comprising polypeptides are linked to an Fc portion of an antibody (i.e., a conjugate comprising an activin-binding domain comprising polypeptide of an ActRII receptor and an Fc portion of an antibody is generated). In certain embodiments, the activin-binding domain is linked to an Fc portion of an antibody via a linker, e.g., a peptide linker. Examples of such non-antibody proteins selected for activin or ActRIIA binding and methods for design and selection of the same are found in WO/2002/088171, WO/2006/055689, WO/2002/032925, WO/2005/037989, US 2003/0133939, and US 2005/0238646, each of which is incorporated herein by reference in its entirety.

Recombinant and mutated forms of GM-CSF can be prepared as described in U.S. Pat. Nos. 5,391,485; 5,393,870; and 5,229,496; the disclosure of each of which is incorporated herein by reference in its entirety. Recombinant and mutated forms of G-CSF can be prepared as described in U.S. Pat. Nos. 4,810,643; 4,999,291; 5,528,823; and 5,580,755; the disclosure of each of which is incorporated herein by reference in its entirety.

This disclosure encompasses the use of native, naturally occurring, and recombinant proteins. The disclosure further encompasses mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., J. Immunol. Methods 248:91-101 (2001).

Antibodies that can be used in combination with Compound 1 provided herein include monoclonal and polyclonal antibodies. Examples of antibodies include, but are not limited to, trastuzumab (HERCEPTIN®), rituximab (RITUXAN®), bevacizumab (AVASTIN™), pertuzumab (OMNITARG™), tositumomab (BEXXAR®), edrecolomab (PANOREX®), panitumumab and G250. Compound 1 provided herein can also be combined with or used in combination with anti-TNF-α antibodies.

Large molecule active agents may be administered in the form of anti-cancer vaccines. For example, vaccines that secrete, or cause the secretion of, cytokines such as IL-2, SCF, CXC14 (platelet factor 4), G-CSF, and GM-CSF can be used in the methods, pharmaceutical compositions, and kits of the disclosure. See, e.g., Emens, L. A., et al., Curr. Opinion Mol. Ther. 3(1):77-84 (2001).

Second active agents that are small molecules can also be used to alleviate adverse effects associated with the administration of Compound 1 provided herein. However, like some large molecules, many are believed to be capable of providing a synergistic effect when administered with (e.g., before, after or simultaneously) the Compound 1.Examples of small molecule second active agents include, but are not limited to, anti-cancer agents, antibiotics, immunosuppressive agents, and steroids.

Examples of anti-cancer agents include, but are not limited to: abraxane; ace-11; acivicin; aclarubicin; acodazole hydrochloride; acronine; adozelesin; aldesleukin; altretamine; ambomycin; ametantrone acetate; amrubicin; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; herceptin; hydroxyurea; idarubicin hydrochloride; ifosfamide; ilmofosine; iproplatin; irinotecan; irinotecan hydrochloride; lanreotide acetate; lapatinib; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; romidepsin; safingol; safingol hydrochloride; semustine; simtrazene; sparfosate sodium; sparsomycin; spirogermanium hydrochloride; spiromustine; spiroplatin; stem cell treatments such as PDA-001; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; b-FGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., GLEEVEC®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim;Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (GENASENSE®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone;

prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; top sentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

In certain embodiments, the second active agent is oblimersen)(GENASENSE®, GM-CSF, G-CSF, SCF, EPO, an anti-CD38 antibody, including daratumumab, SAR650984 and MOR03087, an anti-CD20 antibody, including, rituximab, obinutuzumab, tositumomab,131I tositumomab, 90Y ibritumomab, 111I ibritumomab, ofatumumab, and a mixture thereof, an alkylating agent, including cyclophosphamide (Cytoxan®), chlorambucil, bendamustine (Treanda®) and ifosfamide (Ifex®); a corticosteroid, including prednisone and dexamethasone (Decadron®); a platinum drug, including, cisplatin, carboplatin, and oxaliplatin; a purine analog, including, fludarabine (Fludara®), pentostatin (Nipent®) and cladribine (2-CdA, Leustatin®); an anti-metabolite, including, cytarabine (ara-C), gemcitabine (Gemzar®), methotrexate and palatrexate (Folotyn®); and other anticancer drugs, including, vincristine (Oncovin®), doxorubicin (Adriamycin®), mitoxantrone, etoposide (VP-16) and bleomycin, or a combination thereof In certain embodiments, the second active agent is selected from oblimersen, GM-CSF, G-CSF, SCF, EPO, rituximab, obinutuzumab, tositumomab,131I tositumomab, 90Y ibritumomab, 111I ibritumomab, ofatumumab, brentuximab vedotin, nelarabine, cyclophosphamide, chlorambucil, bendamustine, carmustine, ifosfamide, prednisone, dexamethasone, cisplatin, carboplatin, oxaliplatin, fludarabine, pentostatin, cladribine, cytarabine, gemcitabine, methotrexate, pralatrexate, vincristine, vinblastine sulfate, doxorubicin, mitoxantrone, etoposide, belinostat, bortezomib, denileukin diftitox, ibrutinib, idelalisib, intron A, recombinant interferon Alfa-2b, romidepsin, lenalidomide, mechlorethamine hydrochloride, plerixafor, vorinostat, and bleomycin, or a combination thereof.

In certain embodiments, the second active agent is elotuzmab, luspatercept (ACE-536) or sotatercept (formerly ACE-011).

In one embodiment, the second agent is an anti-CD38 antibody. In one embodiment, the anti-CD38 antibody is daratumumab, SAR650984 or MOR03087.

In certain embodiments, the second active agent is an anti-CD20 antibody selected from obinutuzumab (Gazyva®), rituximab, ibritumomab (Zevalin®), tiuxetan, tositumomab, ofatumumab (Arzerra ®) (Genmab), AME-133v (by Applied Molecular Evolution), ocrelizumab, TRU-015 (by Trubion), and IMMU-106 (veltuzumab).

In certain embodiments, the second active agent is an epigenetic drug. Exemplary epigenetic drugs include DNA demethylating agents such as 5-azacytidine and decitabine, and histone deacetylase (HDAC) inhibitors such as vorinostat and valproic acid.

In certain embodiments, the second active agent is an BTK inhibitor ibrutinib (PCI-32765 and marketed under the name Imbruvica).

In certain embodiments, the second active agent is a proteasome inhibitor MLN9708,ixazomib, bortezomib, carfilzomib, salinosproamide A NPI-0052, ONX 0912, (PR047 or oprozomib), CEP 18770 and epoxomicin.

In certain embodiments, the second active agent is a VEGFR2 inhibitor cabozantinib.

In certain embodiments, the second active agent is a selective BCL-2 inhibitor venetoclax.

In certain embodiments, the second active agent is selected from luspatercept (ACE-536) and sotatercept (formerly ACE-011).

In certain embodiments, the second active agent is an anti-CD20 antibody selected from rituximab, ocrelizumab, GA-101 and ublituximab.

In certain embodiments, the second active agent is an anti-CD22 antibody CTLA4-Ig (abatacept), anti-IL-6 (tocilizumab), epratuzumab, anti-TNFs (etanercept, golimumab, adalimumab, certolizumab), anti-IL-17, anti-BAFF or anti-BLyS (belimumab, and tabalumab), anti-APRIL or atacicept.

In certain embodiments, the second active agent is lambrolizumab, (MK-3475), BMS-936559, atezolizumab, pembrolizumab (Keytruda), Medi7436,nivolumab (BMS-936558, MDX-1106, ONO-4538) or pidilizumab (MDV9300).

In certain embodiments, Compound 1 is administered in combination with cyclophosphamide, doxorubicin hydrochloride, vincristine sulfate, and prednisone.

In certain embodiments, Compound 1 is administered in combination with cyclophosphamide, vincristine sulfate, procarbazine hydrochloride and prednisone.

In certain embodiments, Compound 1 is administered in combination with cyclophosphamide, vincristine sulfate and prednisone.

In certain embodiments, Compound 1 is administered in combination with etoposide, cyclophosphamide, vincristine sulfate, doxorubicin hydrochloride and prednisone.

In certain embodiments, Compound 1 is administered in combination with cyclophosphamide, vincristine sulfate, doxorubicin hydrochloride and dexamethasone.

In certain embodiments, Compound 1 is administered in combination with ifosfamide, carboplatin and etoposide.

In certain embodiments, Compound 1 is administered in combination with rituximab, cyclophosphamide, doxorubicin hydrochloride, vincristine sulfate, and prednisone.

In certain embodiments, Compound 1 is administered in combination with rituximab, cyclophosphamide, vincristine sulfate and prednisone.

In certain embodiments, Compound 1 is administered in combination with rituximab, etoposide, prednisone, vincristine sulfate, cyclophosphamide and doxorubicin hydrochloride.

In certain embodiments, GM-CSF, G-CSF, SCF or EPO is administered subcutaneously during about five days in a four or six week cycle in an amount ranging from about 1 to about 750 mg/m$^2$/day, from about 25 to about 500 mg/m$^2$/day, from about 50 to about 250 mg/m$^2$/day, or from about 50 to about 200 mg/m$^2$/day. In certain embodiments, GM-CSF may be administered in an amount of from about 60 to about 500 mcg/m$^2$ intravenously over 2 hours or from about 5 to about 12 mcg/m$^2$/day subcutaneously. In certain embodiments, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In certain embodiments, EPO may be administered subcutaneously in an amount of 10,000 Unit 3 times per week.

In certain embodiments, Compound 1 is administered in combination with ABT-737 (Abbott Laboratories) and/or obatoclax (GX15-070) to patients with lymphoma.

In certain embodiments, Compound 1 is administered alone or in combination with a second active ingredient such as vinblastine or fludarabine to patients with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

Also encompassed herein is a method of increasing the dosage of an anti-cancer drug or agent that can be safely and effectively administered to a patient, which comprises administering to the patient (e.g., a human) Compound 1. Patients that can benefit by this method are those likely to suffer from an adverse effect associated with anti-cancer drugs for treating lymphoma. The administration of Compound 1 alleviates or reduces adverse effects which are of such severity that it would otherwise limit the amount of anti-cancer drug.

In one embodiment, Compound 1 is administered orally and daily in an amount ranging from about 1 to about 15 mg, from about 1 to about 10 mg, or from about 2 to about 10 mg, prior to, during, or after the occurrence of the adverse effect associated with the administration of an anti-cancer drug to a patient. In certain embodiments, Compound 1 is administered in combination with specific agents such as heparin, aspirin, coumadin, or G-CSF to avoid adverse effects that are associated with anti-cancer drugs such as but not limited to neutropenia or thrombocytopenia.

In another embodiment, encompassed herein is a method of treating, preventing and/or managing lymphoma, which comprises administering Compound 1 in conjunction with (e.g. before, during, or after) conventional therapy including, but not limited to, surgery, immunotherapy, biological therapy, radiation therapy, or other non-drug based therapy presently used to treat, prevent or managelymphoma. The combined use of the compound provided herein and conventional therapy may provide a unique treatment regimen that is unexpectedly effective in certain patients. Without being limited by theory, it is believed that Compound 1 may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, hormonal therapy, biological therapy and immunotherapy. Compound 1 and other active ingredient can be administered to a patient prior to, during, or after the occurrence of the adverse effect associated with conventional therapy.

In one embodiment, Compound 1 can be administered in an amount ranging from about 0.1 to about 50 mg, from about 1 to about 10 mg, or from about 2 to about 5 mg orally and daily alone, or in combination with a second active agent disclosed herein, prior to, during, or after the use of conventional therapy.

5.5.2 Use With Transplantation Therapy

Compound 1 provided herein can be used to reduce the risk of Graft Versus Host Disease (GVHD). Therefore, encompassed herein is a method of treating, preventing and/or managing cancer, which comprises administering Compound 1 in conjunction with transplantation therapy.

As those of ordinary skill in the art are aware, the treatment of lymphoma is often based on the stages and mechanism of the disease. For example, as inevitable leukemic transformation develops in certain stages of cancer, transplantation of peripheral blood stem cells, hematopoietic stem cell preparation or bone marrow may be necessary. The combined use of Compound 1 provided herein and transplantation therapy provides a unique and unexpected synergism. In particular, Compound 1 exhibits immunomodulatory activity that may provide additive or synergistic effects when given concurrently with transplantation therapy in patients.

Compound 1 can work in combination with transplantation therapy reducing complications associated with the invasive procedure of transplantation and risk of GVHD. Encompassed herein is a method of treating, preventing and/or managing lymphoma which comprises administering to a patient (e.g., a human) Compound 1 before, during, or after the transplantation of umbilical cord blood, placental blood, peripheral blood stem cell, hematopoietic stem cell preparation, or bone marrow. Some examples of stem cells suitable for use in the methods provided herein are disclosed in U.S. Pat. No. 7,498,171, the disclosure of which is incorporated herein by reference in its entirety.

In one embodiment, Compound 1 is administered to patients with NHL (e.g., DLBCL) before, during, or after the transplantation of autologous peripheral blood progenitor cell.

In another embodiment, Compound 1 is administered to patients with NHL (e.g., DLBCL) after a stem cell transplantation.

5.6 Pharmaceutical Compositions and Dosage Forms

In one embodiment, provided herein are pharmaceutical compositions and dosage forms, which comprise Compound 1. In another embodiment, pharmaceutical compositions and dosage forms further comprise one or more excipients.

In certain embodiments, pharmaceutical compositions and dosage forms provided herein also comprise one or more additional active ingredients. Consequently, pharmaceutical compositions and dosage forms provided herein comprise Compound 1 and a second active agent. Examples of optional second, or additional, active ingredients are disclosed herein (see, e.g., section 5.5.1).

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal, or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms provided herein may vary depending on their use. For example, a dosage form used in the acute treatment of a disease may contain larger amounts of one or more of the active ingredients than a dosage form used in the chronic treatment of the same disease. Similarly, a parenteral dosage form may contain smaller amounts of one or more of the active ingredients than an oral dosage form used to treat the same disease. See, e.g., *Remington's Pharmaceutical Sciences*, 18th ed., Mack Publishing, Easton Pa. (1990).

Whether a particular excipient is suitable for incorporation into a pharmaceutical composition or dosage form provided herein depends on a variety of factors, including, but not limited to, the route of administration. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, encompassed herein are pharmaceutical compositions and dosage forms that contain little, if any, lactose. As used herein, the term "lactose-free" means that the amount of lactose present, if any, is insufficient to substantially increase the degradation rate of an active ingredient.

Lactose-free compositions provided herein can comprise excipients that are listed, for example, in the *U.S. Pharmacopeia* (USP) 25-NF20 (2002). In certain embodiments, lactose-free compositions comprise active ingredients, a binder/filler, and a lubricant in pharmaceutically compatible and pharmaceutically acceptable amounts. In certain embodiments, lactose-free dosage forms comprise active ingredients, microcrystalline cellulose, pre-gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, New York, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, in certain embodiments, provided herein are anhydrous compositions packaged using materials to prevent exposure to water such that they can be included in suitable formulary kits. Examples of suitable packaging include, but are not limited to, hermetically sealed foils, plastics, unit dose containers (e.g., vials), blister packs, and strip packs.

Encompassed herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In certain embodiments, the dosage forms provided herein comprise Compound 1 in an amount ranging from about 0.10 to about 50 mg, from about 0.10 to about 20 mg, from about 0.10 to about 15 mg, from about 0.10 to about 10 mg, from about 0.10 to about 5 mg, or from about 1 to about 5 mg. In certain embodiments, the dosage forms provided herein comprise Compound 1 in an amount of about 0.1, about 1, about 2, about 5, about 7.5, about 10, about 12.5, about 15, about 17.5, about 20, about 25 mg, about 30 mg, about 40 mg or about 50 mg.

5.6.1 Oral Dosage Forms

In certain embodiments, pharmaceutical compositions provided herein that are suitable for oral administration are formulated as discrete dosage forms, examples of which include, but are not limited to, tablets (e.g., chewable tablets), caplets, capsules, and liquids (e.g., flavored syrups). Such dosage forms contain predetermined amounts of active ingredients and may be prepared by some known methods of pharmacy. See generally, *Remington's Pharmaceutical Sciences,* 18th ed., Mack Publishing, Easton Pa. (1990). Exemplary oral dosage forms for use in the methods provided herein or are described in U.S. Provisional Application No. 62/210, 923, filed Aug. 27, 2015 and US Publication No. 2015/0196562, the disclosures of each of which are incorporated herein by reference in their entireties.

In certain embodiments, the oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms may be prepared by some known methods of pharmacy. In certain embodiments, pharmaceutical compositions and dosage forms are prepared by uniformly and intimately admixing the active ingredients with liquid carriers, finely divided solid carriers, or both, and then shaping the product into the desired presentation if necessary.

In certain embodiments, a tablet is prepared by compression or molding. In certain embodiments, compressed tablets are be prepared by compressing in a suitable machine the active ingredients in a free-flowing form, e.g., powder or granules, optionally mixed with an excipient. In certain embodiments, molded tablets are made by molding in a suitable machine a mixture of a powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms provided herein include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, AVICEL-PH-101, AVICEL-PH-103 AVICEL RC-581, AVICEL-PH-105 (FMC Corporation, American Viscose Division, Avicel Sales, Marcus Hook, Pa.), and mixtures thereof. An specific binder is a mixture of microcrystalline cellulose and sodium carboxymethyl cellulose (e.g., AVICEL RC-581). Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. In certain embodiments, the binder or filler in pharmaceutical compositions provided herein is present in from about 50 to about 99 weight percent of the pharmaceutical composition or dosage form.

Disintegrants are used in the compositions provided herein to provide tablets the ability to disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation. In certain embodiments, the pharmaceutical compositions provided herein comprise from about 0.5 to about 15 weight percent or from about 1 to about 5 weight percent of disintegrant.

Disintegrants that are suitable for use in pharmaceutical compositions and dosage forms provided herein include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that are suitable for use in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, but are not limited to, a syloid silica gel (AEROSIL200, W.R. Grace Co., Baltimore, Md.), a coagulated aerosol of synthetic silica (Degussa Co. of Plano, Tex.), CAB-O-SIL (a pyrogenic silicon dioxide, Cabot Co. of Boston, Mass.), and mixtures thereof. In certain embodiments, if used at all, lubricants are used in an amount of less than about 1 weight percent of the pharmaceutical compositions or dosage forms into which they are incorporated.

In certain embodiments, Compound 1 is administered in an oral dosage form in the form of a capsule which includes Compound 1 at an amount of about 0.5 to about 5 weight percent of the total weight of the composition; a binder or filler at an amount of about 90 to 98 weight percent of total weight of the composition, where the binder or filler is not lactose and a lubricant.

In one embodiment, the oral dosage form of Compound 1 is in the form of a capsule which comprises Compound 1 at an amount of about 0.5 to about 3 weight percent of the total weight of the composition; a binder or filler at an amount of about 90 to 96 weight percent of total weight of the composition, wherein the binder or filler is lactose, silicified microcrystalline cellulose, or a mixture thereof In one embodiment, the oral dosage form of Compound 1 weighs about 50 mg and comprises: Compound 1 at an amount that provides 0.5 mg potency of 3-(5-amino-2-methyl-4-oxo-4H-quinazolin-3-yl)-piperidine-2,6-dione; and a pharmaceutically acceptable carrier or excipient. In one embodiment, the oral dosage form of Compound 1 weighs about 100 mg and comprises: Compound 1 at an amount that provides 1 mg potency of 3-(5-amino-2-methyl-4-oxo-4H-quinazolin-3-yl)-piperidine-2,6-dione; and a pharmaceutically acceptable carrier or excipient. In one embodiment, the oral dosage form of Compound 1 weighs about 300 mg and comprises: Compound 1 at an amount that provides 3 mg potency of 3-(5-amino-2-methyl-4-oxo-4H-quinazolin-3-yl)-piperidine-2,6-dione Compound 1; and a pharmaceutically acceptable carrier or excipient.

In another aspect, the oral dosage form which weighs about 100 mg and includes: Compound 1 at an amount that provides 0.5 mg Compound 1 and a pharmaceutically acceptable carrier or excipient that includes a lubricant. In another aspect the oral dosage form which weighs about 100 mg and includes: Compound 1, at an amount that provides 1 mg Compound 1; and a pharmaceutically acceptable carrier or excipient that includes a lubricant. In yet another, the oral dosage form which weighs about 120 mg and includes: Compound 1, at an amount that provides 3 mg Compound 1and a pharmaceutically acceptable carrier or excipient that includes a lubricant. In still another aspect, the oral dosage form that weighs about 200 mg and includes: Compound 1, at an amount that provides 2 mg Compound 1 and a pharmaceutically acceptable carrier or excipient that includes a lubricant. In another aspect, the oral dosage form which weighs about 140 mg and includes: Compound 1 at an amount that provides 3.5 mg Compound 1; and a pharmaceutically acceptable carrier or excipient that includes a lubricant. In another aspect, the oral dosage form which weighs about 160 mg and includes: Compound 1, at an amount that provides 4 mg Compound 1; and a pharmaceutically acceptable carrier or excipient that includes a lubricant. In yet another aspect, the oral dosage form that weighs about 200 mg and includes: Compound 1, at an amount that provides 5 mg Compound 1 and a pharmaceutically acceptable carrier or excipient that includes a lubricant.

In still another aspect, the oral dosage form includes: Compound 1,at an amount that provides 0.5, 1, 2, 3, 3.5, 4, or 5 mg Compound 1 and a pharmaceutically acceptable carrier or excipient that includes a lubricant.

5.6.2 Delayed Release Dosage Forms

In certain embodiments, the active ingredients provided herein are administered by controlled release means or by delivery devices. Examples include, but are not limited to, those described in U.S. Pat. Nos.: 3,845,770; 3,916,899; 3,536,809; 3,598,123; 4,008,719, 5,674,533, 5,059,595, 5,591,767, 5,120,548, 5,073,543, 5,639,476, 5,354,556, and 5,733,566, each of which is incorporated herein by reference in its entirety. In certain embodiments, such dosage forms are be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Encompassed herein are single unit dosage forms suitable for oral administration, including, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

5.6.3 Parental Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Some suitable vehicles that can be used to provide parenteral dosage forms provided herein include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms provided herein. For example, cyclodextrin and its derivatives can be used to increase the solubility of a compound provided herein, e.g., Compound 1, or an enantiomer or a mixture of enantiomers thereof, or a pharmaceutically acceptable salt, solvate, hydrate, co-crystal, clathrate, or polymorph thereof. See, e.g., U.S. Pat. No. 5,134,127, the disclosure of which is incorporated herein by reference in its entirety.

5.6.4 Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's Pharmaceutical Sciences*, 16$^{th}$ and 18$^{th}$ eds., Mack Publishing, Easton Pa. (1980 & 1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein depend on the particular tissue to which a given pharmaceutical composition or dosage form will be applied. With that fact in mind, in certain embodiments, the excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Additional examples of such ingredients can be found, e.g., in *Remington's Pharmaceutical Sciences*, 16$^{th}$ and 18$^{th}$ eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

5.6.5 Kits

In certain embodiments, active ingredients provided herein are not administered to a patient at the same time or by the same route of administration. Therefore, encompassed herein are kits which, when used by the medical practitioner, can simplify the administration of appropriate amounts of active ingredients to a patient.

In certain embodiments, a kit provided herein comprises a dosage form of a compound provided herein, e.g., Compound 1, or an enantiomer or a mixture of enantiomers thereof, or a pharmaceutically acceptable salt, solvate, hydrate, co-crystal, clathrate, or polymorph thereof. In certain embodiments, the kit provided herein further comprises additional active ingredients, such asoblimersen)(GENASENSE®), GM-CSF, G-CSF, SCF, EPO, an anti-CD20 antibody, including, rituximab, obinutuzumab, tositumomab,131I tositumomab, 90Y ibritumomab, 111I ibritumomab, ofatumumab, and a mixture thereof, an alkylating agent, including cyclophosphamide (Cytoxan®), chlorambucil, bendamustine (Treanda®) and ifosfamide (Ifex®); a corticosteroid, including prednisone and dexamethasone (Decadron®); a platinum drug, including, cisplatin, carboplatin, and oxaliplatin; a purine analog, including, fludarabine (Fludara®), pentostatin (Nipent®) and cladribine (2-CdA, Leustatin®); an anti-metabolite, including, cytarabine (ara-C), gemcitabine (Gemzar®), methotrexate and palatrexate (Folotyn®); and other anticancer drugs, including, vincristine (Oncovin®), doxorubicin (Adriamycin®), mitoxantrone, etoposide (VP-16) and bleomycin, or a combination thereof. Examples of the additional active ingredients include, but are not limited to, those disclosed herein.

In certain embodiments, the kit provided herein further comprises a device that is used to administer the active ingredients. Examples of such devices include, but are not limited to, syringes, drip bags, patches, and inhalers.

In certain embodiments, the kit provided herein further comprises cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

6. EXAMPLES

Certain embodiments of the invention are illustrated by the following non-limiting examples.

6.1 Example 1

Preparation of 3-(5-amino-2-methyl-4-oxo-4h-quinazolin-3-yl)-piperidine-2,6-dione

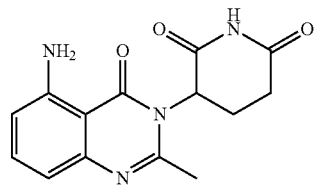 [SMILES: Cc1nc2cccc(N)c2c(=O)n1C1CCC(=O)NC1=O]

Step 1: To a solution of potassium hydroxide (16.1 g, 286 mmol) in water (500 mL), was added 3-nitrophthalimide (25.0 g, 130 mmol) in portion at 0° C. The suspension was stirred at 0° C. for 3 hrs, and then heated to 30° C. for 3 hrs. To the solution, was added HCl (100 mL, 6N). The resulting suspension was cooled to 0° C. for 1 hr. The suspension was filtered and washed with cold water (2×10 mL) to give 3-nitro-phthalamic acid as a white solid (24.6 g, 90% yield): $^1$H NMR (DMSO-$d_6$) δ 7.69 (brs, 1H, NHH), 7.74 (t, J=8 Hz, 1H, Ar), 7.92 (dd, J=1, 8 Hz, 1H, Ar), 8.13 (dd, J=1, 8 Hz, 1H, Ar), 8.15 (brs, 1H, NHH), 13.59 (s, 1H, OH); $^{13}$C NMR (DMSO-$d_6$) δ 125.33, 129.15, 130.25, 132.54, 136.72, 147.03, 165.90, 167.31.

Step 2: To a mixture of 3-nitro-phthalamic acid (24.6 g, 117 mmol) and potassium hydroxide (6.56 g, 117 mmol) in water (118 mL), was added a mixture of bromine (6 mL), potassium hydroxide (13.2 g, 234 mmol) in water (240 mL) at 0° C., followed by addition of a solution of potassium hydroxide (19.8 g, 351 mmol) in water (350 mL). After 5 minutes at 0° C., the mixture was heated in a 100° C. oil bath for 1 hr. The reaction solution was cooled to room temperature, and then, in an ice-water bath for 30 minutes. To the mixture, a solution of HCl (240 mL, 2N) was added dropwise at 0° C., and the resulting mixture was kept for 1 hr. The supsension was filtered and washed with water (5 mL) to give 2-amino-6-nitro-benzoic acid as yellow solid (15.6 g, 73% yield): HPLC: Waters Symmetry $C_{18}$, 5 µm, 3.9×150 mm, 1 mL/min, 240 nm, $CH_3CN$/0.1% $H_3PO_4$, 5% grad to 95% over 5 min, 5.83 min (85%); $^1$H NMR (DMSO-$d_6$) δ 6.90 (dd, J=1, 8 Hz, 1H, Ar), 7.01 (dd, J=1, 9 Hz, 1H, Ar), 7.31 (t, J=8 Hz, 1H, Ar), 8.5-9.5 (brs, 3H, OH, $NH_2$); $^{13}$C NMR (DMSO-$d_6$) δ 105.58, 110.14, 120.07, 131.74, 149.80, 151.36, 166.30;LCMS: MH =183.

Step 3: A mixture of 2-amino-6-nitro-benzoic acid (1.5 g, 8.2 mmol) in acetic anhydride (15 mL) was heated at 200° C. for 30 minutes in a microwave oven. The mixture was filtered and washed with ethyl acetate (20 mL). The filtrate was concentrated in vacuo. The solid was stirred in ether (20 mL) for 2 hrs. The suspension was filtered and washed with ether (20 mL) to give 2-methyl-5-nitro-benzo[d][1,3]oxazin-4-one as a light brown solid (1.4 g, 85% yield): HPLC: Waters Symmetry $C_{18}$, 5 µm, 3.9×150 mm, 1 mL/min, 240 nm, $CH_3CN$/0.1% $H_3PO_4$, 5% grad 95% in 5 min, 5.36 min (92%); $^1$H NMR (DMSO-$d_6$) δ 2.42 (s, 3H, $CH_3$), 7.79 (dd, J=1, 8 Hz, 1H, Ar), 7.93 (dd, J=1, 8 Hz, 1H, Ar), 8.06 (t, J=8 Hz, 1H, Ar); $^{13}$C NMR (DMSO-$d_6$) δ 20.87, 107.79, 121.54, 128.87, 137.19, 147.12, 148.46, 155.18, 161.78; LCMS: MH=207.

Step 4: Two vials each with a suspension of 5-nitro-2-methyl-benzo[d][1,3]oxazin-4-one (0.60 g, 2.91 mmol) and 3-amino-piperidine-2,6-dione hydrogen chloride (0.48 g, 2.91 mmol) in pyridine (15 mL) were heated at 170° C. for 10 minutes in a microwave oven. The suspension was filtered and washed with pyridine (5 mL). The filtrate was concentrated in vacuo. The resulting mixture was stirred in HCl (30 mL, 1N), ethyl acetate (15 mL) and ether (15 mL) for 2 hrs. The suspension was filtered and washed with water (30 mL) and ethyl acetate (30 mL) to give a dark brown solid, which was stirred with methanol (50 mL) at room temperature overnight. The suspension was filtered and washed with methanol to give 3-(2-methyl-5-nitro-4-oxo-4H-quinazolin-3-yl)-piperidine-2,6-dione as a black solid (490 mg, 27% yield). The solid was used in the next step without further purification.

Step 5: A mixture of 3-(2-methyl-5-nitro-4-oxo-4H-quinazolin-3-yl)-piperidine-2,6-dione (250 mg) and Pd(OH)$_2$ on carbon (110 mg) in DMF (40 mL) was shaken under hydrogen (50 psi) for 12 hrs. The suspension was filtered through a pad of Celite and washed with DMF (10 mL). The filtrate was concentrated in vacuo and the resulting oil was purified by flash column chromatography (silica gel, methanol/methylene chloride) to give 3-(5-amino-2-methyl-4-oxo-4H-quinazolin-3-yl)-piperidine-2,6-dione as a white solid (156 mg, 69% yield): HPLC: Waters Symmetry C$_{18}$, 5 μm, 3.9×150 mm, 1 mL/min, 240 nm, 10/90 CH$_3$CN/0.1% H$_3$PO$_4$, 3.52 min (99.9%); mp: 293-295° C.; $^1$H NMR (DMSO-d$_6$) δ 2.10-2.17 (m, 1H, CHH), 2.53 (s, 3H, CH$_3$), 2.59-2.69 (m, 2H, CH$_2$), 2.76-2.89 (m, 1H, CHH), 5.14 (dd, J =6, 11 Hz, 1H, NCH), 6.56 (d, J =8 Hz, 1H, Ar), 6.59 (d, J =8 Hz, 1H, Ar), 7.02 (s, 2H, NH$_2$), 7.36 (t, J=8 Hz, 1H, Ar), 10.98 (s, 1H, NH); $^{13}$C NMR (DMSO-d$_6$) δ 20.98, 23.14, 30.52, 55.92, 104.15, 110.48, 111.37, 134.92, 148.17, 150.55, 153.62, 162.59, 169.65, 172.57; LCMS: MH=287; Anal. Calcd. for C$_{14}$H$_{14}$N$_4$O$_3$+0.3 H$_2$O: C, 57.65; H, 5.05; N, 19.21. Found: C, 57.50; H, 4.73; N, 19.00.

6.2 Example 2

In Vitro Myeloid Differentiation Assay

Human CD34+ bone marrow cells were seeded in stem cell factor, Fms-like tyrosine kinase 3 ligand (Flt3L) and granulocyte colony-stimulating factor (G-CSF), followed by 6 days with media plus G-CSF.

Compound 1 (0.5 mM) was added continuously or on a 5-of-7-day (5/7 d) schedule. After 14 days, myeloid maturation stages were measured by CD34, CD33, and CD11b flow cytometry.

Figure 1:
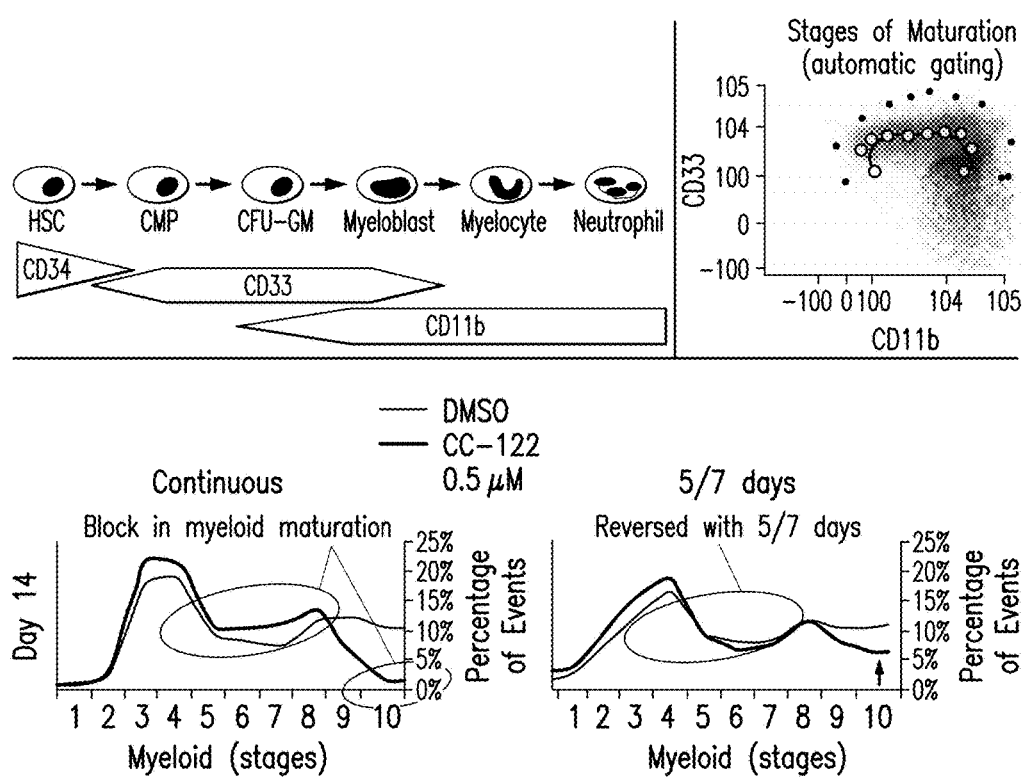

As demonstrated in FIG. 1, continuous exposure to Compound 1 led to reversible myeloid maturation arrest and 90% decreased mature neutrophils compared with vehicle. Compound 1 exposure for 5/7 d resulted in only 50% decreased mature neutrophils.

Thus, in in vitro myeloid differentiation assay, myeloid maturation arrest by Compound 1,possibily due to Ikaros degradation, can be partially bypassed with a 2 day drug holiday.

6.3 Example 3

Clinical Study

The tolerability and clinical activity of Compound 1 were evaluated on intermittent schedules in patients with relapsed or refractory DLBCLA.

Key inclusion criteria included

Documented diagnosis of diffuse large B-cell lymphoma (DLBCL) or mantle cell lymphoma (MCL) (for NHL-1) and DLBCL (for DLBCL-2), Progression on or inability to tolerate standard therapy, ECOG performance status of 0-2, hemoglobin≥9.0 g/dL, ANC≥1.5×10$^9$/L, and Platelets≥60×10$^9$/L.

Key exclusion criteria included symptomatic CNS metastases, peripheral neuropathy grade ≥2, and impaired cardiac function or clinically significant cardiac disease Dosing: Compound 1 was administered orally on 3 different intermittent schedules until disease progression or intolerability:

1. Based on previous experience, patients received 4 mg Compound 1 once daily on days 1-21 of a 28-day cycle (21/28 d)

2. Based on results of the in vitro myeloid differentiation assay described in Example 2, patients received 4 mg of Compound 1 on days 1-5 of a 7-day cycle continuously (5/7 d), or 3. Based on results of the in vitro myeloid differentiation assay described in Example 2, patients received 5 mg of Compound 1 on days 1-5 of a 7-day cycle continuously (5/7 d).

Adverse events (AEs) were graded by NCI CTCAE v4.0, and responses were investigator assessed using International Workshop criteria for NHL.

Sample Analysis

Aiolos was measured by flow cytometry on samples of whole blood drawn at 0 hours (pre-dose) and at 1.5 and 5 hours post-dose on cycle 1, day 1

Archival or screening formalin-fixed paraffin-embedded (FFPE) tissues were stained for MYC and BCL2 expression6 on a Bond-Max automated slide stainer (Leica Microsystems, Buffalo Grove, Ill.)

Pathology review was performed on a hematoxylin and eosin stained slides to identify the area of DLBCL RNA extraction and NanoString nCounter Analysis System lymphoma subtyping test (Seattle, Wash.) were performed as reported previously7 on core needle and excisional biopsy samples For lymphocyte phenotyping, whole blood was drawn pre-dose (baseline) and 1.5 hours post-dose on cycle 1 day 15, cycle 1 day 22, cycle 2 day 15, and cycle 2 day 22

Memory T cells (CD3+/CD4+/CD8/CD45RA−/CD45RO+ and CD3+/CD4+/CD8/CD45RA−/CD45RO+) were measured by flow cytometry.

Patient Characteristics and Safety Profile 25 patients were enrolled in NHL-1, of which 23 were efficacy evaluable Among these evaluable patients, 22 had DLBCL and 1 had MCL 29 patients were enrolled in DLBCL-2, of which 23 were efficacy evaluable Table 1 below provides patient characteristics and safety profile.

TABLE 1

| Characteristics | NHL-1 3 mg qd (n = 25) | DLBCL-2 4 mg 5/7 d (n = 21) |
|---|---|---|
| Male, n (%) | 16 (64) | 9 (43) |
| Median age, years (range) | 64 (31-83) | 62 (38-91) |
| Age >65 years, n (%) | 11 (44) | 7 (33) |
| ECOG performance status 0/1/2, % | 40/44/16 | 19/71/10 |
| Median time since diagnosis, months (range) | 17.3 (4.2-127.0) | 19.5 (6.0-85.9) |
| Median prior systemic therapy, n (range) | 4 | 3 |
| Prior ASCT, n (%) | 4 (16) | 4 (19) |
| Response to last therapy, n (%) | | |
| CR/PR | 8 (32) | 6 (29) |
| SD/PD | 13 (52) | 13 (62) |
| Response to R-CHOP <CR, n (%) | 5 (20) | 6 (29) |
| Relapse <6 months since last treatment, n (%) | 19 (76) | 17 (81) |

ASCT, autologous stem cell transplant;
CR, complete response;
DLBCL, diffuse large B-cell lymphoma,
ECOG, Eastern Cooperative Oncology Group;
PD, progressive disease, rituximab plus cyclosphosphamide, doxorubicin, vincristine, and prednisone;
SD, stable disease.

Dose-Limiting Toxicities:

Patients treated with 4 mg Compound 1 in the 21/28 d cohort (n=3) experienced no dose-limiting toxicities (DLTs) during cycle 1 (see Table 2). All 3 patients, however, required subsequent dose reduction due to grade 4 neutropenia. Therefore, this dose level was considered the non-tolerated dose (NTD) for the 21/28 d schedule.

The NTD for the 5/7 d schedule was 5 mg (see Table 2).

The MTD of Compound 1 for the 5/7 d schedule of 4 mg was selected for this study. 21 Patients have been enrolled in the DLBCL-2 expansion study. No DLTs were reported in the 19 DLT-evaluable patients Table 2 below summarizes dose-limiting toxicities:

TABLE 2

| | NHL-1 | DLBCL-2 | | |
|---|---|---|---|---|
| | 3 mg qd | 4 mg 5/7 d | 4 mg 21/28 d | 5 mg 5/7 d |
| DLT evaluable, n | 18 | 19 | 3 | 5 |
| DLTs, n (%) | 3 (17) | 0 | 0 | 2 (40) |
| DLTs | Grade 3 febrile neutropenia Grade 4 sepsis Grade 4 neutropenia | Grade 4 neutropenia | — | Grade 3 Febrile neutropenia Grade 3 pneumonitis |

DLT, dose-limiting toxicity; qd. once daily.

Adverse Events (AEs):

In patients receiving 4 mg 5/7 d, the most common AEs were pyrexia (57%), neutropenia (52%), and asthenia and constipation (29% each) (see Table 3). 3 Patients (14%) experienced serious treatment-related AEs: neck pain, pneumonia, and pneumonitis (5% each). Treatment-related AEs resulted in study discontinuation in 3 patients (14%). Table 3 below summarizes AEs.

TABLE 3

| | AEs Occurring in >20% of Patients | | Grade 3/4 AEs Occurring in >1 Patient | |
|---|---|---|---|---|
| Adverse events, n (%) | 3 mg 28/28 d (n = 25) | 4 mg 5/7 d (n = 21) | 3 mg 28/28 d (n = 25) | 4 mg 5/7 d (n = 21) |
| Hematologic | | | | |
| Neutropenia | 19 (76) | 11 (52) | 16 (64) | 8 (38) |
| Anemia | 13 (52) | 5 (24) | 3 (12) | 0 |
| Thrombocytopenia | 9 (36) | 5 (21) | 3 (12) | 0 |
| Nonhematologic | | | | |
| Asthenia | 14 (56) | 6 (29) | 5 (20) | 0 |
| Cough | 10 (40) | 2 (10) | 0 | 0 |
| Pyrexia | 10 (40) | 12 (57) | 0 | 0 |
| Peripheral edema | 7 (28) | 4 (19) | 0 | 0 |
| Diarrhea | 5 (20) | 3 (14) | 0 | 0 |
| Constipation | 4 (16) | 6 (29) | 0 | 0 |
| Dyspnea | 4 (16) | 5 (24) | 0 | 0 |
| Nausea | 4 (16) | 5 (24) | 0 | 0 |
| Vomiting | 4 (16) | 5 (24) | 0 | 0 |
| Decreased Appetite | 3 (12) | 3 (14) | 0 | 0 |
| | 1 (4) | 3 (14) | 0 | 0 |
| Arrhythmia | 0 | 2 (10) | 0 | 2 (7) |

Dose Modifications, Interruptions, and Exposure are summarized in Table 4 and explained below"
  Dose modifications: 29% of patients in the 4 mg 5/7 d group experienced 1 dose reduction and 14% discontinued treatment due to AEs
  Median relative dose intensity was 97.5% for the 4 mg 5/7 d cohort (see Table 4)
  Among patients treated with 3 mg Compound 1 daily continuously (n=25), the median relative dose intensity was 78.6%.

TABLE 4

| Variable | 3 mg 28/28 d (n = 25) | 4 mg 5/7 d (n = 21) |
|---|---|---|
| Patients with ≥1 reduction n (%) | 11 (44) | 6 (29) |
| Discontinuations due to AE, n (%) | 5 (20) | 3 (14) |
| Relative dose intensity, % (range) | 78.6 (41-100) | 97.5 (65-100) |
| Patients with ≥1 dose G-CSF n (%) | 17 (68) | 6 (29) |

Figure 2:
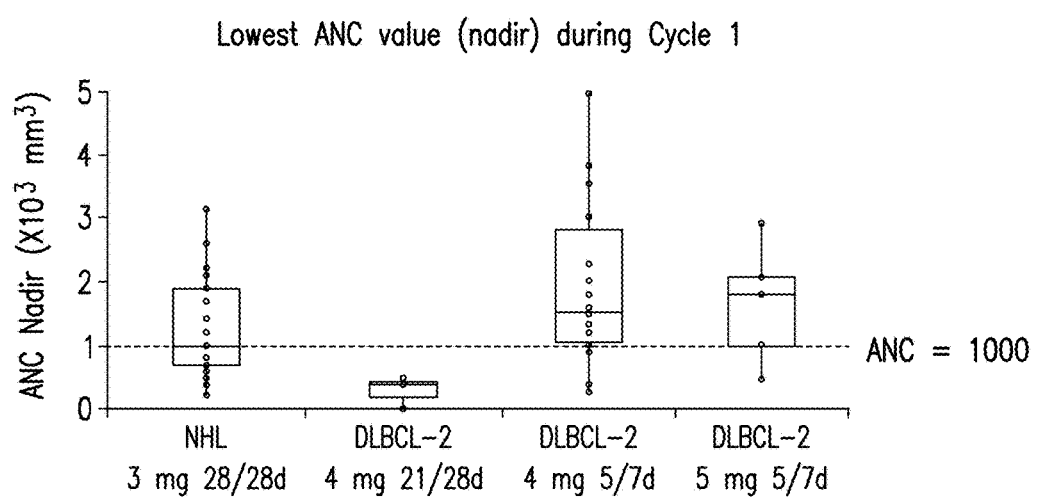

As demonstrated in FIG. 2, severity of neutropenia was mitigated in 5/7 d schedule.

Figure 3:
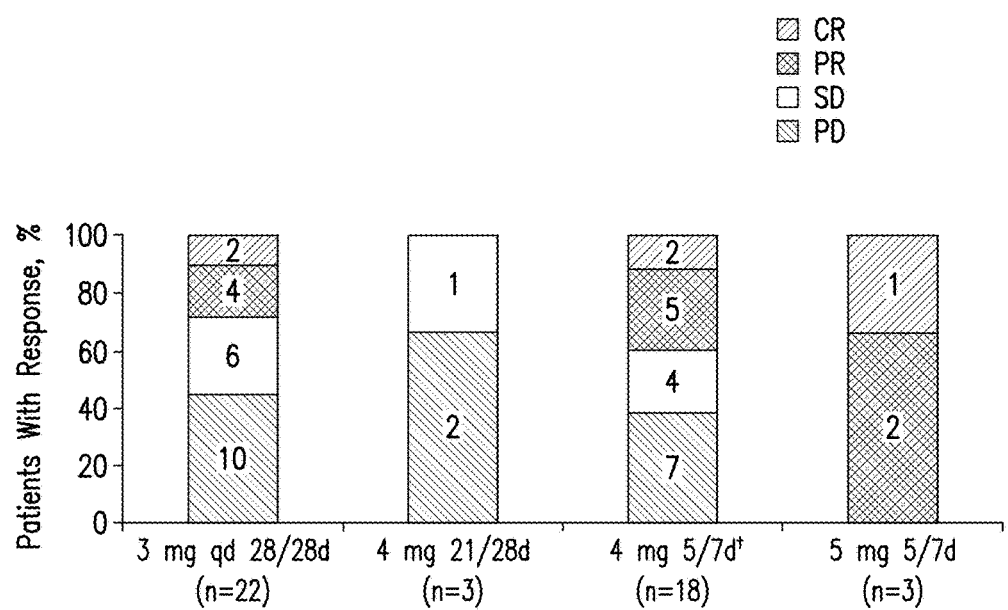
FIG. 3 illustrates response to treatment with 3-(5-amino-2-methyl-4-oxo-4H-quinazolin-3-yl)-piperidine-2,6-dione for the efficacy-evaluable population. Number of patients with response is shown within the bars.

Responses to 21/28 and 5/7 treatments in the efficacy-evaluable population are provided in FIG. 3. The number of patients with response is shown within the bars.
  In the 3 mg 28/28 d cohort (n=22), overall response rate (ORR) was 27% (2 complete responses [CR], 4 partial responses [PR]).
  In the 4 mg 5/7 d DLBCL-2 cohort (n=17), ORR was 39% (2 CR, 5 PR).
  There were no responses among the 3 patients in the 4 mg 21/28 d DLBCL-2 cohort.
  In the 5 mg 5/7 d DLBCL-2 cohort (n=3), ORR was 100% (1 CR, 2 PR).

Figure 4:
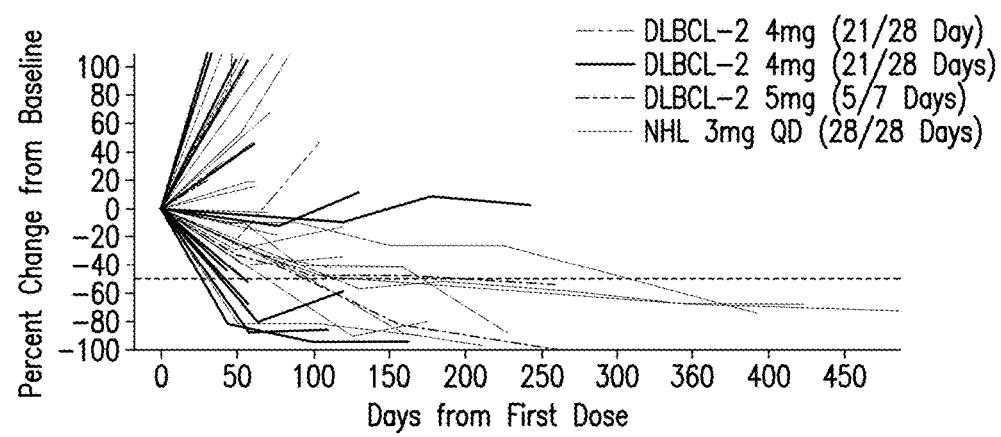
FIG. 4 illustrates change from baseline by dose level of 3-(5-amino-2-methyl-4-oxo-4H-quinazolin-3-yl)-piperidine-2,6-dione.

FIG. 4 illustrates change from baseline in SPD by dose level.

As demonstrated in FIG. 5, degradation of Aiolos by Compound 1 is comparable on 5/7 d vs. daily dosing schedule. The median change in Aiolos levels relative to baseline in peripheral T cells when measured 5 hours post-dosing on cycle 1, days 1, 10, and 22,was −47%, −28%, and −47%, respectively (see FIG. 5). These results indicate that Aiolos degradation occurs throughout the 5/7 d treatment cycle and is comparable to daily dosing. No dose-dependent Aiolos degradation was observed at the 3, 4, or 5 mg doses.

As demonstrated in FIG. 6, Compound 1 increases memory effector T-Cell populations on 5/7 d schedule. The median increase from baseline in helper memory T cells and cytotoxic memory T cells at cycle 1,day 22,in peripheral blood was 75% and 266%, respectively.

Responses to Compound 1 as determined by 50% reduction in tumor size were observed in both MYC/BCL2-positive and -negative disease (see Table 5,FIG. 7A). Compound 1 is active in both MYC/BCL2 dual expressors and non-expressors. Response rates in the MYC/BCL2-positive and -negative populations were 30% and 23%, respectively.

TABLE 5

| Biomarker | ORR | PFS, days |
| --- | --- | --- |
| MYC/BCL2 dual expressor | | |
| Negative | 6/20 (30%) | 70 |
| Positive | 3/13 (23%) | 100 |
| Cell of Origin | | |
| ABC | 4/10 (40%) | 99 |
| GCB | 6/19 (32%) | 100 |
| Unclassified | 2/8 (25%) | 51 |
| Non-ABC | 8/27 (30%) | 64 |
| Non-GCB | 6/18 (33%) | 74 |

Responses to Compounds 1 as determined by 50% reduction in tumor size were observed in Activated B Cell (ABC), Germinal Center B Cell (GCB), and unclassified DLBCL (see Table 5,FIG. 7B). Compound 1 is active in ABC, GCB, and unclassified cell of origin. Response rates in ABC, GCB, and unclassified populations were 40%, 32%, and 25%, respectively.

Clinical exploration of intermittent dosing confirmed that 5/7 d schedule mitigated neutropenia-related dose reductions and may improve Compound 1 clinical activity in relapse/refractory DLBCL patients. The study demonstrates that Compound 1 has activity in a cell of origin independent manner. In addition, the immunomodulatory effects of Compound 1 are maintained on the 5/7 d schedule.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method for treating, managing, and/or ameliorating lymphoma, while reducing an adverse effect associated with such treating, managing, and/or ameliorating, said method comprising administering to a patient in need thereof an effective amount of compound 3-(5-amino-2-methyl-4-oxo-4H-quinazolin-3-yl)-piperidine-2,6-dione, which has the following structure:

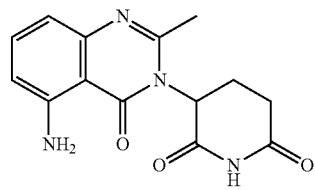 [SMILES: Cc1nc2cccc(N)c2c(=O)n1C1CCC(=O)NC1=O]

or a pharmaceutically acceptable salt, solvate, hydrate, polymorph, stereoisomer, tautomer or racemic mixture thereof, wherein the compound is administered to said subject in a cycling therapy, said cycling therapy comprising:
   an administration period of 5 days followed by a rest period of 2 days.

2. The method of claim 1, wherein the compound is a solvate of 3-(5-amino-2-methyl-4-oxo-4H-quinazolin-3-yl)-piperidine-2,6-dione.

3. The method of claim 1, wherein the compound is a hydrate of 3-(5-amino-2-methyl-4-oxo-4H-quinazolin-3-yl)-piperidine-2,6-dione.

4. The method of claim 1, wherein the compound is a pharmaceutically acceptable salt of 3-(5-amino-2-methyl-4-oxo-4H-quinazolin-3-yl)-piperidine-2,6-dione.

5. The method of claim 1, wherein the compound is 3-(5-amino-2-methyl-4-oxo-4H-quinazolin-3-yl)-piperidine-2,6-dione.

6. The method of claim 1, wherein the adverse effect comprises neutropenia.

7. The method of claim 1, wherein the compound is administered orally.

8. The method of claim 1, wherein the compound is administered at a dose of about 1 mg to about 5 mg.

9. The method of claim 8, wherein the dose is about 3 mg or about 4mg.

10. The method of claim 8, wherein the dose is about 4 mg.

11. The method of claim 8, wherein the dose is about 3 mg.

12. The method of claim 1, wherein the cycling therapy is repeated 2 to 6times.

13. The method of claim 1, wherein the method further comprises co-administering a second therapeutic agent.

14. The method of claim 13, wherein said second therapeutic agent is selected from oblimersen, GM-CSF, G-CSF, SCF, EPO, rituximab, obinutuzumab, tositumomab,131I tositumomab, 90Y ibritumomab, 111I ibritumomab, ofatumumab, brentuximab vedotin, nelarabine, cyclophosphamide, chlorambucil, bendamustine, carmustine, ifosfamide, prednisone, dexamethasone, cisplatin, carboplatin, oxaliplatin, fludarabine, pentostatin, cladribine, cytarabine, gemcitabine, methotrexate, pralatrexate, vincristine, vinblastine sulfate, doxorubicin, mitoxantrone, etoposide, belinostat, bortezomib, denileukin diftitox, ibrutinib, idelalisib, intron A, recombinant interferon Alfa-2b, romidepsin, lenalidomide, mechlorethamine hydrochloride, plerixafor, vorinostat, and bleomycin, or a combination thereof.

15. The method of claim 1, wherein the lymphoma is non-Hodgkin lymphoma.

16. The method of claim 1, wherein the lymphoma is diffuse large B-cell lymphoma.

17. The method of claim 16, wherein the diffuse large B-cell lymphoma is activated B-cell type.

18. The method of claim 16, wherein the diffuse large B-cell lymphoma is germinal center B-cell type.

19. The method of claim 16, wherein the diffuse large B-cell lymphoma is of unclassified cell of origin.

20. The method of claim 16, wherein the diffuse large B-cell lymphoma is relapsed or refractory.

21. The method of claim 1, wherein the lymphoma is mantle cell lymphoma.

22. The method of claim 1, wherein the lymphoma is relapsed or refractory.

* * * * *